US010369187B2

(12) United States Patent
Gurevich et al.

(10) Patent No.: US 10,369,187 B2
(45) Date of Patent: Aug. 6, 2019

(54) PEPTIDE REGULATORS OF JNK FAMILY KINASES

(71) Applicant: Vanderbilt University, Nashville, TN (US)

(72) Inventors: Vsevolod V. Gurevich, Nashville, TN (US); Eugenia V. Gurevich, Nashville, TN (US); Xuanzhi Zhan, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 15/892,853

(22) Filed: Feb. 9, 2018

(65) Prior Publication Data

US 2018/0236026 A1 Aug. 23, 2018

Related U.S. Application Data

(60) Provisional application No. 62/456,828, filed on Feb. 9, 2017.

(51) Int. Cl.
*A61K 38/10* (2006.01)
*C07K 19/00* (2006.01)
*A61K 38/17* (2006.01)

(52) U.S. Cl.
CPC .......... *A61K 38/10* (2013.01); *A61K 38/1709* (2013.01)

(58) Field of Classification Search
None
See application file for complete search history.

(56) References Cited

U.S. PATENT DOCUMENTS

| | | | |
|---|---|---|---|
| 4,122,193 | A | 10/1978 | Scherm et al. |
| 4,273,774 | A | 6/1981 | Scherm |
| 4,895,841 | A | 1/1990 | Sugimoto et al. |
| 5,061,703 | A | 10/1991 | Bormann |
| 5,985,864 | A | 11/1999 | Imai et al. |
| 6,140,321 | A | 10/2000 | Imai et al. |
| 6,245,911 | B1 | 6/2001 | Imai et al. |
| 6,372,760 | B1 | 4/2002 | Kato et al. |

OTHER PUBLICATIONS

Ahmed, M. R. et al. Ubiquitin ligase parkin promotes Mdm2-arrestin interaction but inhibits arrestin ubiquitination. Biochemistry 50, 3749-3763 (2011).
Breitman, M. et al. Silent scaffolds: inhibition of c-Jun N-terminal kinase 3 activity the cell by a dominant-negative arrestin-3 mutant. J Biol Chem 287, 19653-19664 (2012).
Bruchas, M. R., Macey, T. A., Lowe, J. D. & Chavkin, C. Kappa opioid receptor activation of p38 MAPK is GRK3- and arrestin-dependent in neurons and astrocytes. J Biol Chem 281, 18081-18089 (2006).
Burack, W. R. & Shaw, A. S. Signal transduction: hanging on a scaffold. Curr Opin Cell Biol 12, 211-216 (2000).
Carman, C. V. & Benovic, J. L. G-protein-coupled receptors: turn-ons and turn-offs. Curr Opin Neurobiol 8, 335-344 (1998).
Davis, R. J. Signal transduction by the JNK group of MAP kinases. Cell 103, 239-252 (2000).
Dhanasekaran, D. N., Kashef, K., Lee, C. M., Xu, H. & Reddy, E. P. Scaffold proteins of MAP-kinase modules. Oncogene, 3185-3202 (2007).
Els, S., Beck-Sickinger, A. G. & Chollet, C. Ghrelin receptor: high constitutive activity and methods for developing inverse agonists. Methods Enzymol 485, 103-121 (2010).
Flemming, A. Alzheimer's Disease: JNK3 as new target in AD? Nat Rev Drug Discov 11, 829 (2012).
Good, M. C., Zalatan, J. G. & Lim, W. A. Scaffold proteins: hubs for controlling the flow of cellular information. Science 332, 680-686 (2011).
Gurevich, E. V. & Gurevich, V. V. Arrestins are ubiquitous regulators of cellular signaling pathways. Genome Biol 7, 236 (2006).
Gurevich, V. V. & Gurevich, E. V. The structural basis of arrestin-mediated regulation of G protein-coupled receptors. Pharm Ther 110, 465-502 (2006).
Han, M., Gurevich, V. V., Vishnivetskiy, S. A., Sigler, P. B. & Schubert, C. Crystal structure of beta-arrestin at 1.9 A: possible mechanism of receptor binding and membrane translocation. Structure 9, 869-880 (2001).
Hanson, S. M. et al. Arrestin mobilizes signaling proteins to the cytoskeleton and redirects their activity. J Mol Biol 368, 375-387 (2007).
Hirsch, J. A., Schubert, C., Gurevich, V. V. & Sigler, P. B. The 2.8 A crystal structure of visual arrestin: a model for arrestin's regulation. Cell 97, 257-269 (1999).
Kang, Y. et al. Crystal structure of rhodopsin bound to arrestin determined by femtosecond X-ray laser. Nature 523, 561-567 (2015).
Keshet, Y. & Seger, R. The MAP kinase signaling cascades: a system of hundreds of components regulates a diverse array of physiological functions. Methods Mol Biol 661, 3-38 (2010).
Kim, M. et al. Conformation of receptor-bound visual arrestin. Proc Nat Acad Sci USA 109, 18407-18412 (2012).
Kook, S. et al. Arrestin-3 binds JNK1α1 and JNK2α2 and facilitates the activation of these ubiquitous JNK isoforms in cells via scaffolding. J Biol Chem 288, 37332-37342 (2013).
Lawler, S., Fleming, Y., Goedert, M. & Cohen, P. Synergistic activation of SAPK1/JNK1 by two MAP kinase kinases in vitro. Curr Biol 8, 1387-1390 (1998).
Levchenko, A., Bruck, J. & Sternberg, P. W. Regulatory modules that generate biphasic signal response in biological systems. Syst Biol (Stevenage) 1, 139-148 (2004).
Levchenko, A., Bruck, J. & Sternberg, P. W. Scaffold proteins may biphasically affect the levels of mitogen-activated protein kinase signaling and reduce its threshold properties. Proc Natl Acad Sci U S A 97, 5818-5823 (2000).
Lim, W. A. Designing customized cell signalling circuits. Nat Rev Mol Cell Biol 11, 393-403 (2010).

(Continued)

*Primary Examiner* — John D Ulm
(74) *Attorney, Agent, or Firm* — Meunier Carlin & Curfman LLC

(57) ABSTRACT

The present disclosure relates to the fields of proliferative disorders (for example, cancer) and disorders associated with excessive cell death (for example, neurodegenerative disorders).

4 Claims, 10 Drawing Sheets

Specification includes a Sequence Listing.

(56) References Cited

OTHER PUBLICATIONS

Luttrell, L. M. et al. Activation and targeting of extracellular signal-regulated kinases by beta-arrestin scaffolds. Proc Natl Acad Sci U S A 98, 2449-2454 (2001).

McDonald, P. H. et al. Beta-arrestin 2: a receptor-regulated MAPK scaffold for the activation of JNK3. Science 290, 1574-1577 (2000).

Miller, W. E. et al. Identification of a motif in the carboxyl terminus of beta-arrestin2 responsible for activation of JNK3. J Biol Chem 276, 27770-27777 (2001).

Sabapathy, K. Role of the JNK pathway in human diseases. Prog Mol Biol Transl Sci 106, 145-169 (2012).

Seo, J., Tsakem, E. L., Breitman, M. & Gurevich, V. V. Identification of arrestin-3-specific residues necessary for JNK3 activation. J Biol Chem 286, 27894-27901 (2011).

Song, X., Coffa, S., Fu, H. & Gurevich, V. V. How does arrestin assemble MAPKs into a signaling complex? J Biol Chem 284, 685-695, doi:M806124200 [pii]10.1074/jbc.M806124200 (2009).

Song, X., Raman, D., Gurevich, E. V., Vishnivetskiy, S. A. & Gurevich, V. V. Visual and both non-visual arrestins in their "inactive" conformation bind JNK3 and Mdm2 and relocalize them from the nucleus to the cytoplasm. J Biol Chem 281, 21491-21499 (2006).

Sterne-Marr, R. et al. Polypeptide variants of beta-arrestin and arrestin3. J Biol Chem 268, 15640-15648 (1993).

Sutton, R. B. et al. Crystal Structure of Cone Arrestin at 2.3Å: Evolution of Receptor Specificity. J Mol Biol 354, 1069-1080 (2005).

Widmann, C., Gibson, S., Jarpe, M. B. & Johnson, G. L. Mitogen-activated protein kinase: conservation of a three-kinase module from yeast to human. Physiol Rev 79, 143-180 (1999).

Yasuda, J., Whitmarsh, A. J., Cavanagh, J., Sharma, M. & Davis, R. J. The JIP group of mitogen-activated protein kinase scaffold proteins. Mol Cell Biol 19, 7245-7254 (1999).

Yoon, S. O. et al. JNK3 perpetuates metabolic stress induced by Aβ peptides. Neuron 75, 824-837 (2012).

Zhan, et al., "Arrestin-3 binds the MAP kinase JNK3α2 via multiple sites on both domains", Cell Signal. 26(4): 766-776 (2014).

Zhan, X. et al. Arrestin-3-Dependent Activation of c-Jun N-Terminal Kinases (JNKs). Curr Protoc Pharmacol 68, 2.12.11-12.12.26 (2015).

Zhan, X., Gimenez, L. E., Gurevich, V. V. & Spiller, B. W. Crystal structure of arrestin-3 reveals the basis of the difference in receptor binding between two non-visual arrestins. J Mol Biol 406, 467-478 (2011).

Zhan, X., Kaoud, T. S., Dalby, K. N. & Gurevich, V. V. Non-visual arrestins function as simple scaffolds assembling MKK4-JNK3α2 signaling complex. Biochemistry 50, 10520-10529 (2011).

Zhan, X., Kaoud, T. S., Kook, S., Dalby, K. N. & Gurevich, V. V. JNK3 binding to arrestin-3 differentially affects the recruitment of upstream MAP kinase kinases. J Biol Chem 288, 28535-28547 (2013).

Zhuang, T. et al. Involvement of Distinct Arrestin-1 Elements in Binding to Different Functional Forms of Rhodopsin. Proc Nat Acad Sci USA 110, 942-947 (2013).

(SEQ ID NO:27) JNK3 activator (T16) Ac-KIKKVKKKGRKGGG-GLYVTLKCNPSSKKFV-NH2
(SEQ ID NO:28) JNK3 inhibitor (T15) Ac-KIKKVKKKGRKGGG-VTLKCNPSSKKFVRT-NH2
FIG. 12
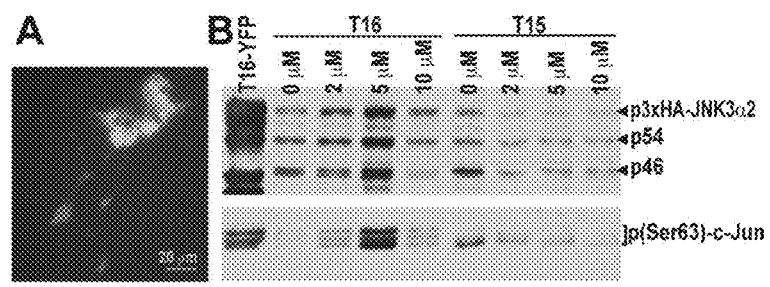
FIG. 13
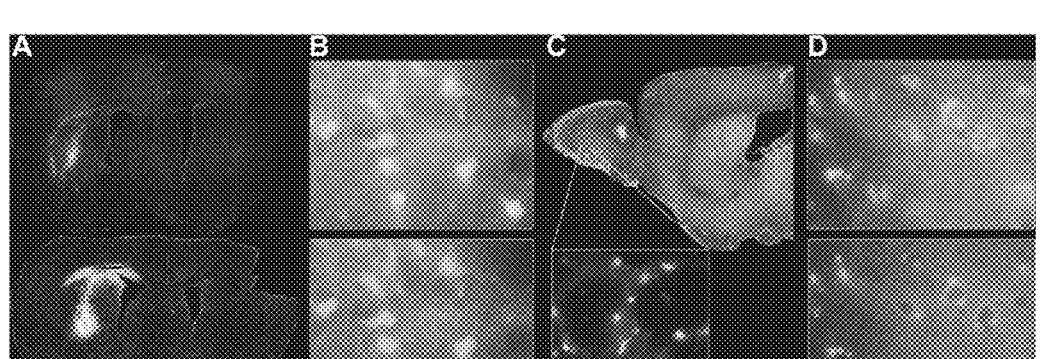
FIG. 14

SEQUENCE LISTING

```
<160> NUMBER OF SEQ ID NOS: 30

<210> SEQ ID NO 1
<211> LENGTH: 25
<212> TYPE: PRT
<213> ORGANISM: bovine

<400> SEQUENCE: 1

Met Gly Glu Lys Pro Gly Thr Arg Val Phe Lys Lys Ser Ser Pro Asn
1               5                   10                  15

Cys Lys Leu Thr Val Tyr Leu Gly Lys
            20                  25

<210> SEQ ID NO 2
<211> LENGTH: 14
<212> TYPE: PRT
<213> ORGANISM: bovine

<400> SEQUENCE: 2
```

```
Lys Lys Ser Ser Pro Asn Cys Lys Leu Thr Val Tyr Leu Gly
1               5                   10
```

<210> SEQ ID NO 3
<211> LENGTH: 15
<212> TYPE: PRT
<213> ORGANISM: bovine

<400> SEQUENCE: 3

```
Thr Arg Val Phe Lys Lys Ser Ser Pro Asn Cys Lys Leu Thr Val
1               5                   10                  15
```

<210> SEQ ID NO 4
<211> LENGTH: 16
<212> TYPE: PRT
<213> ORGANISM: bovine

<400> SEQUENCE: 4

```
Val Phe Lys Lys Ser Ser Pro Asn Cys Lys Leu Thr Val Tyr Leu Gly
1               5                   10                  15
```

<210> SEQ ID NO 5
<211> LENGTH: 13
<212> TYPE: PRT
<213> ORGANISM: bovine

<400> SEQUENCE: 5

```
Val Phe Lys Lys Ser Ser Pro Asn Cys Lys Leu Thr Val
1               5                   10
```

<210> SEQ ID NO 6
<211> LENGTH: 24
<212> TYPE: PRT
<213> ORGANISM: bovine

<400> SEQUENCE: 6

```
Met Gly Asp Lys Gly Thr Arg Val Phe Lys Lys Ala Ser Pro Asn Gly
1               5                   10                  15

Lys Leu Thr Val Tyr Leu Gly Lys
                20
```

<210> SEQ ID NO 7
<211> LENGTH: 420
<212> TYPE: PRT
<213> ORGANISM: bovine

<400> SEQUENCE: 7

```
Met Gly Glu Lys Pro Gly Thr Arg Val Phe Lys Lys Ser Ser Pro Asn
1               5                   10                  15

Cys Lys Leu Thr Val Tyr Leu Gly Lys Arg Asp Phe Val Asp His Leu
                20                  25                  30

Asp Lys Val Asp Pro Val Asp Gly Val Val Leu Val Asp Pro Asp Tyr
            35                  40                  45

Leu Lys Asp Arg Lys Val Phe Val Thr Leu Thr Cys Ala Phe Arg Tyr
    50                  55                  60

Gly Arg Glu Asp Leu Asp Val Leu Gly Leu Ser Phe Arg Lys Asp Leu
65                  70                  75                  80

Phe Ile Ala Asn Tyr Gln Ala Phe Pro Pro Thr Pro Asn Pro Pro Arg
                85                  90                  95

Pro Pro Thr Arg Leu Gln Glu Arg Leu Leu Arg Lys Leu Gly Gln His
                100                 105                 110
```

-continued

```
Ala His Pro Phe Phe Phe Thr Ile Pro Gln Asn Leu Pro Cys Ser Val
            115                 120                 125

Thr Leu Gln Pro Gly Pro Glu Asp Thr Gly Lys Ala Cys Gly Val Asp
130                 135                 140

Phe Glu Ile Arg Ala Phe Cys Ala Lys Ser Leu Glu Glu Lys Ser His
145                 150                 155                 160

Lys Arg Asn Ser Val Arg Leu Val Ile Arg Lys Val Gln Phe Ala Pro
                165                 170                 175

Glu Lys Pro Gly Pro Gln Pro Ser Ala Glu Thr Thr Arg His Phe Leu
            180                 185                 190

Met Ser Asp Arg Ser Leu His Leu Glu Ala Ser Leu Asp Lys Glu Leu
            195                 200                 205

Tyr Tyr His Gly Glu Pro Leu Asn Val Asn Val His Val Thr Asn Asn
    210                 215                 220

Ser Thr Lys Thr Val Lys Lys Ile Lys Val Ser Val Arg Gln Tyr Ala
225                 230                 235                 240

Asp Ile Cys Leu Phe Ser Thr Ala Gln Tyr Lys Cys Pro Val Ala Gln
                245                 250                 255

Val Glu Gln Asp Asp Gln Val Ser Pro Ser Ser Thr Phe Cys Lys Val
            260                 265                 270

Tyr Thr Ile Thr Pro Leu Leu Ser Asn Asn Arg Glu Lys Arg Gly Leu
            275                 280                 285

Ala Leu Asp Gly Lys Leu Lys His Glu Asp Thr Asn Leu Ala Ser Ser
            290                 295                 300

Thr Ile Val Lys Glu Gly Ala Asn Lys Glu Val Leu Gly Ile Leu Val
305                 310                 315                 320

Ser Tyr Arg Val Lys Val Lys Leu Val Val Ser Arg Gly Gly Asp Val
                325                 330                 335

Ser Val Glu Leu Pro Phe Val Leu Met His Pro Lys Pro His Asp His
            340                 345                 350

Ile Ala Leu Pro Arg Pro Gln Ser Ala Ala Thr His Pro Pro Thr Leu
            355                 360                 365

Leu Pro Ser Ala Val Pro Glu Thr Asp Ala Pro Val Asp Thr Asn Leu
            370                 375                 380

Ile Glu Phe Glu Thr Asn Tyr Ala Thr Asp Asp Ile Val Phe Glu
385                 390                 395                 400

Asp Phe Ala Arg Leu Arg Leu Lys Gly Leu Lys Asp Glu Asp Tyr Asp
                405                 410                 415

Asp Gln Phe Cys
            420

<210> SEQ ID NO 8
<211> LENGTH: 25
<212> TYPE: PRT
<213> ORGANISM: bovine

<400> SEQUENCE: 8

Lys Gly Leu Tyr Val Thr Leu Lys Cys Asn Pro Ser Ser Lys Lys Phe
1               5                   10                  15

Val Arg Thr Gly Pro Lys Glu Gly Met
            20                  25

<210> SEQ ID NO 9
<211> LENGTH: 14
<212> TYPE: PRT
<213> ORGANISM: bovine
```

<400> SEQUENCE: 9

Gly Leu Tyr Val Thr Leu Lys Cys Asn Pro Ser Ser Lys Lys
1               5                   10

<210> SEQ ID NO 10
<211> LENGTH: 15
<212> TYPE: PRT
<213> ORGANISM: bovine

<400> SEQUENCE: 10

Val Thr Leu Lys Cys Asn Pro Ser Ser Lys Lys Phe Val Arg Thr
1               5                   10                  15

<210> SEQ ID NO 11
<211> LENGTH: 16
<212> TYPE: PRT
<213> ORGANISM: bovine

<400> SEQUENCE: 11

Gly Leu Tyr Val Thr Leu Lys Cys Asn Pro Ser Ser Lys Lys Phe Val
1               5                   10                  15

<210> SEQ ID NO 12
<211> LENGTH: 13
<212> TYPE: PRT
<213> ORGANISM: bovine

<400> SEQUENCE: 12

Val Thr Leu Lys Cys Asn Pro Ser Ser Lys Lys Phe Val
1               5                   10

<210> SEQ ID NO 13
<211> LENGTH: 24
<212> TYPE: PRT
<213> ORGANISM: bovine

<400> SEQUENCE: 13

Lys Gly Leu Tyr Val Thr Leu Lys Gly Asn Pro Ser Ala Lys Lys Phe
1               5                   10                  15

Val Arg Thr Gly Lys Asp Gly Met
            20

<210> SEQ ID NO 14
<211> LENGTH: 25
<212> TYPE: PRT
<213> ORGANISM: Artificial Sequence
<220> FEATURE:
<223> OTHER INFORMATION: synthetic construct; all amino acids are D
      amino acids

<400> SEQUENCE: 14

Lys Gly Leu Tyr Val Thr Leu Lys Cys Asn Pro Ser Ser Lys Lys Phe
1               5                   10                  15

Val Arg Thr Gly Pro Lys Glu Gly Met
            20                  25

<210> SEQ ID NO 15
<211> LENGTH: 14
<212> TYPE: PRT
<213> ORGANISM: Artificial Sequence
<220> FEATURE:
<223> OTHER INFORMATION: synthetic construct; all amino acids are D
      amino acids

```
<400> SEQUENCE: 15

Gly Leu Tyr Val Thr Leu Lys Cys Asn Pro Ser Ser Lys Lys
1               5                   10

<210> SEQ ID NO 16
<211> LENGTH: 15
<212> TYPE: PRT
<213> ORGANISM: Artificial Sequence
<220> FEATURE:
<223> OTHER INFORMATION: synthetic construct; all amino acids are D
      amino acids

<400> SEQUENCE: 16

Val Thr Leu Lys Cys Asn Pro Ser Ser Lys Lys Phe Val Arg Thr
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: synthetic construct; all amino acids are D
      amino acids

<400> SEQUENCE: 17

Gly Leu Tyr Val Thr Leu Lys Cys Asn Pro Ser Ser Lys Lys Phe Val
1               5                   10                  15

<210> SEQ ID NO 18
<211> LENGTH: 13
<212> TYPE: PRT
<213> ORGANISM: Artificial Sequence
<220> FEATURE:
<223> OTHER INFORMATION: synthetic construct; all amino acids are D
      amino acids

<400> SEQUENCE: 18

Val Thr Leu Lys Cys Asn Pro Ser Ser Lys Lys Phe Val
1               5                   10

<210> SEQ ID NO 19
<211> LENGTH: 24
<212> TYPE: PRT
<213> ORGANISM: Artificial Sequence
<220> FEATURE:
<223> OTHER INFORMATION: synthetic construct; all amino acids are D
      amino acids

<400> SEQUENCE: 19

Lys Gly Leu Tyr Val Thr Leu Lys Gly Asn Pro Ser Ala Lys Lys Phe
1               5                   10                  15

Val Arg Thr Gly Lys Asp Gly Met
            20

<210> SEQ ID NO 20
<211> LENGTH: 14
<212> TYPE: PRT
<213> ORGANISM: bovine

<400> SEQUENCE: 20

Lys Ile Lys Lys Val Lys Lys Gly Arg Lys Gly Gly Gly
1               5                   10

<210> SEQ ID NO 21
<211> LENGTH: 39
<212> TYPE: PRT
```

<213> ORGANISM: Artificial Sequence
<220> FEATURE:
<223> OTHER INFORMATION: synthetic construct; KIKKVKKKGR KGGG are L
amino acids and KGLYVT LKCNPSSKKF VRTGPKEGM are D amino acids

<400> SEQUENCE: 21

Lys Ile Lys Lys Val Lys Lys Lys Gly Arg Lys Gly Gly Gly Lys Gly
1               5                   10                  15

Leu Tyr Val Thr Leu Lys Cys Asn Pro Ser Ser Lys Lys Phe Val Arg
            20                  25                  30

Thr Gly Pro Lys Glu Gly Met
        35

<210> SEQ ID NO 22
<211> LENGTH: 28
<212> TYPE: PRT
<213> ORGANISM: Artificial Sequence
<220> FEATURE:
<223> OTHER INFORMATION: synthetic construct; KIKKVKKKGR KGGG are L
amino acids and GLYVTL KCNPSSKK are D amino acids

<400> SEQUENCE: 22

Lys Ile Lys Lys Val Lys Lys Lys Gly Arg Lys Gly Gly Gly Gly Leu
1               5                   10                  15

Tyr Val Thr Leu Lys Cys Asn Pro Ser Ser Lys Lys
            20                  25

<210> SEQ ID NO 23
<211> LENGTH: 29
<212> TYPE: PRT
<213> ORGANISM: Artificial Sequence
<220> FEATURE:
<223> OTHER INFORMATION: synthetic construct; KIKKVKKKGR KGGG are L
amino acids and VTLKCN PSSKKFVRT are D amino acids

<400> SEQUENCE: 23

Lys Ile Lys Lys Val Lys Lys Lys Gly Arg Lys Gly Gly Gly Val Thr
1               5                   10                  15

Leu Lys Cys Asn Pro Ser Ser Lys Lys Phe Val Arg Thr
            20                  25

<210> SEQ ID NO 24
<211> LENGTH: 30
<212> TYPE: PRT
<213> ORGANISM: Artificial Sequence
<220> FEATURE:
<223> OTHER INFORMATION: synthetic construct; KIKKVKKKGR KGGG are L
amino acids and GLYVTL KCNPSSKKFV are D amino acids

<400> SEQUENCE: 24

Lys Ile Lys Lys Val Lys Lys Lys Gly Arg Lys Gly Gly Gly Gly Leu
1               5                   10                  15

Tyr Val Thr Leu Lys Cys Asn Pro Ser Ser Lys Lys Phe Val
            20                  25                  30

<210> SEQ ID NO 25
<211> LENGTH: 27
<212> TYPE: PRT
<213> ORGANISM: Artificial Sequence
<220> FEATURE:
<223> OTHER INFORMATION: synthetic construct; KIKKVKKKGR KGGG are L
amino acids and VTLKCN PSSKKFV are D amino acids

<400> SEQUENCE: 25

Lys Ile Lys Lys Val Lys Lys Lys Gly Arg Lys Gly Gly Gly Val Thr

```
                1               5                  10                  15
Leu Lys Cys Asn Pro Ser Ser Lys Lys Phe Val
            20                  25

<210> SEQ ID NO 26
<211> LENGTH: 38
<212> TYPE: PRT
<213> ORGANISM: Artificial Sequence
<220> FEATURE:
<223> OTHER INFORMATION: synthetic construct; KIKKVKKKGR KGGG are L
      amino acids and KGLYVT LKGNPSAKKF VRTGKDGM are D amino acids

<400> SEQUENCE: 26

Lys Ile Lys Lys Val Lys Lys Gly Arg Lys Gly Gly Gly Lys Gly
1               5                  10                  15

Leu Tyr Val Thr Leu Lys Gly Asn Pro Ser Ala Lys Lys Phe Val Arg
            20                  25                  30

Thr Gly Lys Asp Gly Met
        35

<210> SEQ ID NO 27
<211> LENGTH: 30
<212> TYPE: PRT
<213> ORGANISM: Artificial Sequence
<220> FEATURE:
<223> OTHER INFORMATION: Synthetic construct

<400> SEQUENCE: 27

Lys Ile Lys Lys Val Lys Lys Gly Arg Lys Gly Gly Gly Leu
1               5                  10                  15

Tyr Val Thr Leu Lys Cys Asn Pro Ser Ser Lys Lys Phe Val
            20                  25                  30

<210> SEQ ID NO 28
<211> LENGTH: 29
<212> TYPE: PRT
<213> ORGANISM: Artificial Sequence
<220> FEATURE:
<223> OTHER INFORMATION: Synthetic construct

<400> SEQUENCE: 28

Lys Ile Lys Lys Val Lys Lys Gly Arg Lys Gly Gly Gly Val Thr
1               5                  10                  15

Leu Lys Cys Asn Pro Ser Ser Lys Lys Phe Val Arg Thr
            20                  25

<210> SEQ ID NO 29
<211> LENGTH: 10
<212> TYPE: PRT
<213> ORGANISM: Artificial Sequence
<220> FEATURE:
<223> OTHER INFORMATION: Synthetic construct

<400> SEQUENCE: 29

Thr Leu Val Pro Arg Gly Ser Pro Gly Phe
1               5                  10

<210> SEQ ID NO 30
<211> LENGTH: 10
<212> TYPE: PRT
```

```
-continued

<213> ORGANISM: Artificial Sequence
<220> FEATURE:
<223> OTHER INFORMATION: Synthetic construct

<400> SEQUENCE: 30

Pro Gly Arg Leu Glu Arg Pro His Arg Asp
1               5                   10
```

PEPTIDE REGULATORS OF JNK FAMILY KINASES

CROSS REFERENCE TO RELATED APPLICATIONS

This application claims the benefit of U.S. Provisional Patent Application Ser. No. 62/456,828, filed Feb. 9, 2017, the disclosure of which is expressly incorporated herein by reference.

STATEMENT REGARDING FEDERALLY SPONSORED RESEARCH

This invention was made with Government Support under Grant No. R01 GM077561 awarded by the National Institutes of Health. The Government has certain rights to the invention.

FIELD

The present disclosure relates to the fields of proliferative disorders (for example, cancer) and disorders associated with excessive cell death (for example, neurodegenerative disorders).

BACKGROUND

The spatial and temporal organization of proteins within a cell is critical for coordinating essential activities. Appropriate cellular response to external or internal stimuli often requires precise orchestration by scaffold proteins, which determine the specificity and precise time course of signaling. In particular, the specificity of signal transduction through mitogen activated protein kinase (MAPK) cascades is highly dependent on scaffold proteins. MAPK signaling is involved in the regulation of key cellular behaviors, from proliferation to differentiation and apoptotic death. The overall architecture of three-kinase MAPK cascades is conserved from yeast to mammals. Most cells have multiple MAPKs, MAPK kinases (MAPKKs), and MAPKK kinases (MAPKKKs), so signaling outcome is often determined by scaffolds organizing particular MAPKKK-MAPKK-MAPK complexes.

The c-Jun $NH_2$-terminal protein kinases (JNKs) belong to the MAPK family. JNKs regulate normal physiological processes of cell proliferation, apoptosis, differentiation, and migration. JNKs were also implicated in many diseases, from cancer to neurological and immunological disorders. Full activation of all JNKs requires double phosphorylation of the T-X-Y motif in the activation loop by two upstream kinases, MKK4 (tyrosine) and MKK7 (threonine). Similar to other MAPKs, JNK activation is dependent on scaffolding proteins. Arrestins, which specifically bind active phosphorylated G protein-coupled receptors (GPCRs), were first discovered as negative regulators of GPCR signaling via G proteins. Among the four arrestin subtypes expressed in vertebrates, only arrestin-3 promotes the activation of JNK3, as well as ubiquitous JNK1/2 in cells, acting as a scaffold that brings together MAPKKK ASK1, MAPKKs MKK4 and MKK7, and several isoforms of JNK1/2/3. What is needed are peptides or compounds that can be used to regulate the JNK3 pathway and to treat cellular proliferative disorders.

The compounds, compositions, and methods disclosed herein address these and other needs.

SUMMARY

Disclosed herein are novel polypeptide compounds and compositions derived from arrestin-3. The inventors have identified novel fragments of the arrestin-3 protein that unexpectedly possess opposite activities (activation vs. inhibition of JNK3 activity). Also disclosed herein are compounds and compositions that inhibit JNK3 activity and are useful in methods for the treatment of a neurodegenerative disease or dyskinesia. Further disclosed are compounds and compositions that facilitate JNK3 activity and are useful in methods for the treatment of a cancer.

In one aspect, disclosed herein is a composition comprising a pharmaceutically acceptable carrier and an isolated polypeptide comprising an amino acid sequence set forth in SEQ ID NO:3.

In one aspect, provided herein is a method of treating a neurodegenerative disease in a subject in need thereof, comprising administering to the subject a composition comprising a pharmaceutically acceptable carrier and an isolated polypeptide comprising an amino acid sequence set forth in SEQ ID NO:3.

In one embodiment, the polypeptide is linked to a second polypeptide, wherein the second polypeptide improves cell permeability of the polypeptide. In one embodiment, the composition further comprises an additional therapeutic agent.

In one embodiment, the neurodegenerative disease is selected from Alzheimer's disease, Parkinson's disease, or dyskinesia. In one embodiment, the neurodegenerative disease is Alzheimer's disease. In one embodiment, the neurodegenerative disease is Parkinson's disease. In one embodiment, the neurodegenerative disease is dyskinesia.

In another aspect, provided herein is a method of treating dyskinesia in a subject in need thereof, comprising administering to the subject a composition comprising a pharmaceutically acceptable carrier and an isolated polypeptide comprising a pharmaceutically acceptable carrier and an isolated polypeptide comprising an amino acid sequence set forth in SEQ ID NO:3.

In one aspect, disclosed herein is a composition comprising a pharmaceutically acceptable carrier and an isolated polypeptide comprising an amino acid sequence set forth in SEQ ID NO:4.

In yet another aspect, disclosed herein is a method of treating a cancer in a subject in need thereof, comprising administering to the subject a composition comprising a pharmaceutically acceptable carrier and an isolated polypeptide comprising an amino acid sequence set forth in SEQ ID NO:4.

In one embodiment, the polypeptide is linked to a second polypeptide, wherein the second polypeptide improves cell permeability of the polypeptide. In one embodiment, the composition further comprises an additional therapeutic agent.

BRIEF DESCRIPTION OF THE DRAWINGS

The accompanying figures, which are incorporated in and constitute a part of this specification, illustrate several aspects described below.

FIG. 12. Cell-permeable arrestin-3-derived peptides modulating JNK3 activity in cells. The beginning sequence ensures cell permeability (derived from [1]). It is made of L-amino acids, so that upon entering cells it can be eliminated by cytoplasmic peptidases to prevent peptide escape from the cell and its targeting to the nucleus. The bold underlined sequence is made of D-amino acids to confer peptidase resistance. The sequence is reversed compared to arrestin-3 to create a perfect retro-inverso mimic of the T1A15 (inhibitor) or T1A16 (activator) sequence. Sequences shown include KIKKVKKKGRKGGG-GLY-VTLKCNPSSKKFV (SEQ ID NO:27) and KIKKVKKK-GRKGGG-VTLKCNPSSKKFVRT (SEQ ID NO:28).

FIG. 13. Cell-penetrating ARR3-derived peptides enter the cells and affect the JNK activity. (A) Differentiated neuronal Neuro2a cells showing accumulated fluorescein-tagged T1A16 after 10 h of incubation. (B) HEK293 cells with endogenous arrestins deleted by CRISPR technology were treated with different concentrations of cell-penetrating T1A16 or T1A15 for 24 h before being lysed and probed for phospho-JNK (upper blot) and phospho-c-Jun (lower blot). Note that high (10 μM) concentration of activating T1A16 showed an inhibitory effect, consistent with the bell curve dose response characteristic of scaffolds, as shown previously for ARR3 [3]. The inhibitory peptide T1A15, which acts as a dominant negative, shows a dose-depend effect particularly evident on p-c-Jun. Left lanes—samples from cells transfected with T1A16-YFP. Note a much stronger effect on pJNK3 but comparable to cpT1A16 on p-c-Jun. p3×HA-JNKα2—doubly phosphorylated JNKα2 with triple HA tag; 3×HA-JNKα2 was transfected into HEK293 cells, since they do not express JNK3.

FIG. 14. Localization of cell-penetrating T1A15 in neurons upon injection into the striatum. CpT1A15 conjugated with fluorescein (cpT1A15-FL) was stereotaxically injected into the caudate-putamen, the mouse sacrificed 3 days after the injection, the brain post-fixed in 4% paraformaldehyde, sectioned, mounted on glass slides, and direct fluorescence of FL observed under Nikon LC2000 fluorescent microscope on brain sections counterstained with DAPI. (A) Low power photomicrograph of the mouse brain coronal sections showing the location of the injection track and the spread of cpT1A15-FL. The upper image—1 μl of 1 mM solution of cpT1A15-FL was injected; the lower image—3 μl. (B) High power photomicrograph of neurons that have taken up cpT1A15-FL; upper panel—an overlay of FL and DAPI images, lower panel—FL image alone. Note the concentration of cpT1A15-FL in the nuclei. (C) A sagittal section of the mouse brain hemisphere ipsilateral to the side of intranasal injection of 3 μl of cpT1A15-FL. The section was counterstained with DAPI. The insert shows the accumulation of the label in the glomerular cells of the olfactory bulb. (D) High power photomicrograph of neurons that have taken up cpT1A15-FL; upper panel—an overlay of FL and DAPI images, lower panel—FL image alone. Note a much lower concentration of the label in neurons as compared to the striatal injection. Also note that the nuclei are essentially free from the fluorescence.

DETAILED DESCRIPTION

Figure 1:
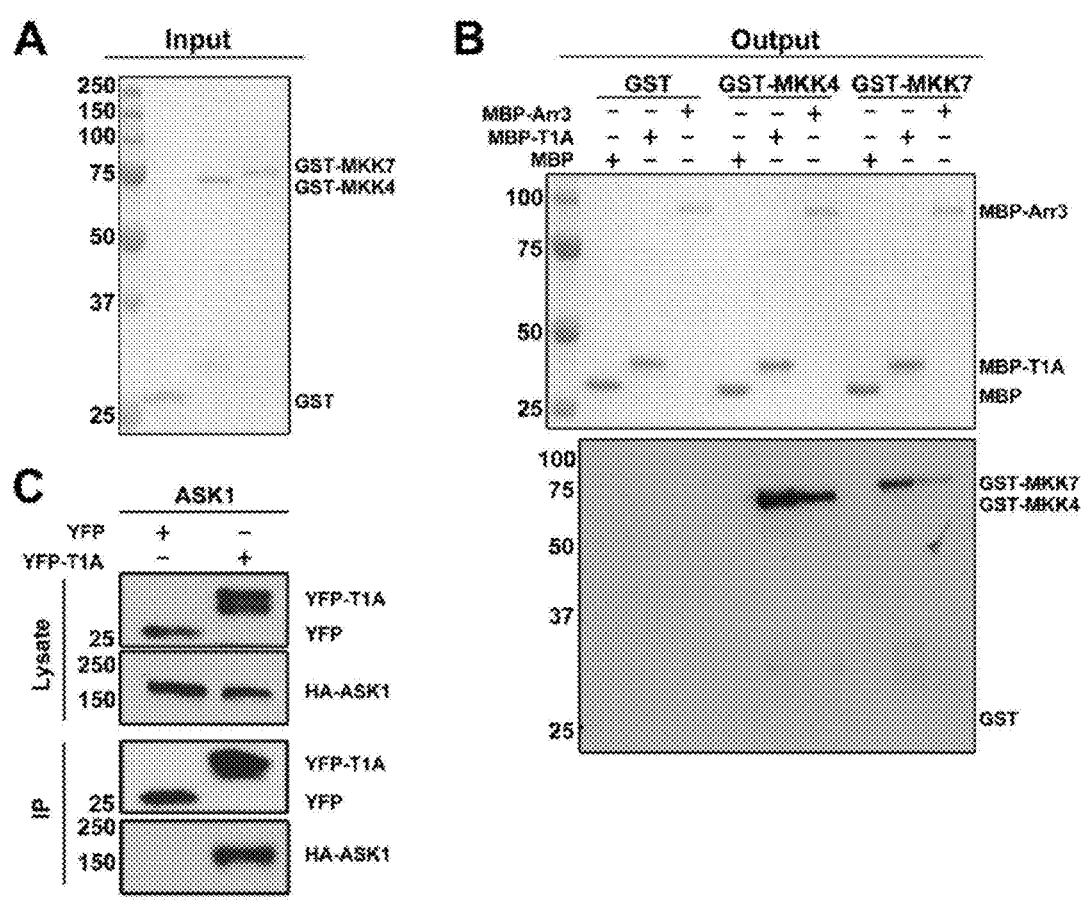
FIG. 1. The T1A peptide binds ASK1, MKK4, and MKK7. a) Purified GST (control), GST-MKK4, and GST-MKK7 (Coomassie staining). b) Top: Coomassie staining of MBP (control), MBP-T1A, and MBP-arrestin-3 bait eluted from amylose beads. Lower blot: GST-MKK4 and GST-MKK7 retained by MBP-T1A and MBP-arrestin-3. Pull-down was performed as described in methods. c) HA-ASK1 was co-immunoprecipitated with YFP-T1A, but not the YFP control, from cells coexpressing these proteins (top blots: lysate; bottom blots: proteins immunoprecipitated with anti-GFP antibody).

Disclosed herein are novel compounds and compositions derived from arrestin-3. The inventors have identified novel fragments of the arrestin-3 protein that unexpectedly possess opposite activities (activation vs. inhibition of JNK3 activity). Also disclosed herein are compounds and compositions that inhibit JNK3 activity and are useful in methods for the treatment of a neurodegenerative disease or dyskinesia. Further disclosed are compounds and compositions that facilitate JNK3 activity and are useful in methods for the treatment of a cancer.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

As used in the specification and claims, the singular form "a," "an," and "the" include plural references unless the context clearly dictates otherwise. For example, the term "a cell" includes a plurality of cells, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition. The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

As used herein, the terms "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount."

However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject.

The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

As used herein, the term "mixture" can include solutions in which the components of the mixture are completely miscible, as well as suspensions and emulsions, in which the components of the mixture are not completely miscible.

As used herein, the term "subject" or "host" can refer to living organisms such as mammals, including, but not limited to humans, livestock, dogs, cats, and other mammals. Administration of the therapeutic agents can be carried out at dosages and for periods of time effective for treatment of a subject. In some embodiments, the subject is a human.

As used herein, the term "controlled-release" or "controlled-release drug delivery" or "extended release" refers to release or administration of a drug from a given dosage form in a controlled fashion in order to achieve the desired pharmacokinetic profile in vivo. An aspect of "controlled" drug delivery is the ability to manipulate the formulation and/or dosage form in order to establish the desired kinetics of drug release.

The phrases "concurrent administration", "administration in combination", "simultaneous administration" or "administered simultaneously" as used herein, means that the compounds are administered at the same point in time or immediately following one another. In the latter case, the two compounds are administered at times sufficiently close that the results observed are indistinguishable from those achieved when the compounds are administered at the same point in time.

The term "polypeptide" refers to a compound made up of a single chain of D- or L-amino acids or a mixture of D- and L-amino acids joined by peptide bonds.

Compounds

In some embodiments, short polypeptides from the N-terminal region of the arrestin-3 peptide were found to have surprising effects on the regulation of JNK activity. In one embodiment, disclosed herein is a polypeptide comprising less than 23 amino acids (for example, 5, 6, 7, 8, 9, 10, 11, 12, 13, 14, 15, 16, 17, 18, 19, 20, 21, 22, or 23 amino acids) from SEQ ID NO:7 (Arrestin-3 (bovine) full sequence).

In one embodiment, disclosed herein are polypeptides selected from the amino acid sequences set forth in SEQ ID NO:1, SEQ ID NO:2, SEQ ID NO:3, SEQ ID NO:4, SEQ ID NO:5, or SEQ ID NO:6. In one embodiment, the polypeptide is SEQ ID NO:1. In one embodiment, the polypeptide is SEQ ID NO:2. In one embodiment, the polypeptide is SEQ ID NO:3. In one embodiment, the polypeptide is SEQ ID NO:4. In one embodiment, the polypeptide is SEQ ID NO:5. In one embodiment, the polypeptide is SEQ ID NO:6.

In some embodiments, the following polypeptide sequences are provided (discussed in further detail in the examples below):

```
                                          (SEQ ID NO: 1)
T1A (arrestin-3)    MGEKPGTRVFKKSSPNCKLTVYLGK (SEQ ID NO: 2)
T1A14 (T1(11-24))         KKSSPNCKLTVYLG (SEQ ID NO: 3)
T1A15 (T1(7-21))            TRVFKKSSPNCKLTV (SEQ ID NO: 4)
T1A16 (T1(9-24))             VFKKSSPNCKLTVYLG (SEQ ID NO: 5)
T1A13 (T1(9-21))             VFKKSSPNCKLTV (SEQ ID NO: 6)
B1A (arrestin-2)    MGDK-GTRVFKKASPNGKLTVYLGK
```

In some embodiments, the polypeptides disclosed herein can act as activators of JNK family kinases. In some embodiments, the polypeptides disclosed herein can act as inhibitors of JNK family kinases. Surprisingly, very small changes to the peptide compounds results in contrasting modes of action.

In some embodiments, the polypeptides can be modified to make them more resistant to proteases. In some embodiments, the polypeptides can be modified to make them more cell-permeable.

In some embodiments, disclosed herein are polypeptides selected from an amino acid sequence that is at least 50% (for example, at least 50%, at least 55%, at least 60%, at least 65%, at least 70%, at least 75%, at least 80%, at least 85%, at least 90%, at least 95%, or more) identical to a sequence selected from SEQ ID NO:1, SEQ ID NO:2, SEQ ID NO:3, SEQ ID NO:4, SEQ ID NO:5, or SEQ ID NO:6.

Additional variations of these peptide sequences herein contemplated for use in the present invention include minor insertions and deletions. Conservative amino acid replacements are contemplated. Such replacements are, for example, those that take place within a family of amino acids that are related in the chemical nature of their side chains. The families of amino acids include the basic charged amino acids (lysine, arginine, histidine); the acidic charged amino acids (aspartic acid, glutamic acid); the non-polar amino adds (glycine, alanine, valine, leucine, isoleucine, proline, phenylalanine, tryptophan); the uncharged polar amino acids (asparagine, methionine, glutamine, cysteine, serine, threonine, tyrosine); and the aromatic amino acids (phenylalanine, tryptophan and tyrosine). In particular, it is generally accepted that conservative amino acid replacements consisting of an isolated replacement of a leucine with an isoleucine or valine, or an aspartic acid with a glutamic acid, or a threonine with a serine, or a similar conservative replacement of an amino acid with a structurally related amino acid will not have a major effect on the properties of the peptide.

In some embodiments, disclosed herein is a synthetic peptide analogue of a native peptide, wherein said synthetic peptide analogue is retro-inverso modified to contain all D-amino acids with reversed direction of peptide bonds and reversed termini, with respect to the native peptide. In some embodiments, the retro-inverso modified peptide is at least five amino acids in length and induces the production of antibodies which recognize the native peptide antigen.

The ability of any retro-inverso (RI) peptide comprising the sequence that is retro-inverso with respect to the sequences disclosed herein, or insertions, deletions or substitutions thereof, to effect JNK activity (inhibition or activation), to provide treatment of a neurodegenerative disease, or to provide treatment for a cancer, can be determined using the assays provided in the examples presented below. In some embodiments, the polypeptides can be modified to create a sequence that is retro-inverso with respect to the sequences disclosed herein. A retro-inverso analogue has reversed termini and reversed direction of peptide bonds while approximately maintaining the topology of the side chains as in the native peptide sequence. Partial retro-inverso peptide analogues are polypeptides in which only part of the sequence is reversed and replaced with enantiomeric amino acid residues. Processes for synthesis of retro-inverso peptide analogues (Bonelli et al., 1984; Verdini and Viscomi, 1985) and some processes for the solid-phase synthesis of partial retro-inverso peptide analogues have been described (Pessi et al., 1987).

In some embodiments, the retro-inverso peptides can be selected from:

(SEQ ID NO: 8)
KGLYVTLKCNPSSKKFVRTGPKEGM, (SEQ ID NO: 9)
GLYVTLKCNPSSKK, (SEQ ID NO: 10)
VTLKCNPSSKKFVRT, (SEQ ID NO: 11)
GLYVTLKCNPSSKKFV, (SEQ ID NO: 12)
VTLKCNPSSKKFV,
or (SEQ ID NO: 13)
KGLYVTLKGNPSAKKFVRTGKDGM.

In some embodiments, the retro-inverso peptides comprise all D amino acids.

In some embodiments, disclosed herein are polypeptides selected from an amino acid sequence that is at least 50% (for example, at least 50%, at least 55%, at least 60%, at least 65%, at least 70%, at least 75%, at least 80%, at least 85%, at least 90%, at least 95%, or more) identical to a sequence selected from SEQ ID NO:8, SEQ ID NO:9, SEQ ID NO:10, SEQ ID NO:11, SEQ ID NO:12, or SEQ ID NO:13.

In some embodiments, the retro-inverso peptides can be selected from:

(SEQ ID NO: 14)
D-Lys-Gly-D-Leu-D-Tyr-D-Val-D-Thr-D-Leu-D-Lys-D-Cys-D-Asn-D-Pro-D-Ser-D-Ser-D-Lys-D-Lys-D-Phe-D-Val-D-Arg-D-Thr-Gly-D-Pro-D-Lys-D-Glu-Gly-D-Met;

(SEQ ID NO: 15)
D-Gly-D-Leu-D-Tyr-D-Val-D-Thr-D-Leu-D-Lys-D-Cys-D-Asn-D-Pro-D-Ser-D-Ser-D-Lys-D-Lys;

(SEQ ID NO: 16)
D-Val-D-Thr-D-Leu-D-Lys-D-Cys-D-Asn-D-Pro-D-Ser-D-Ser-D-Lys-D-Lys-D-Phe-D-Val-D-Arg-D-Thr;

(SEQ ID NO: 17)
D-Gly-D-Leu-D-Tyr-D-Val-D-Thr-D-Leu-D-Lys-D-Cys-D-Asn-D-Pro-D-Ser-D-Ser-D-Lys-D-Lys-D-Phe-D-Val;

(SEQ ID NO: 18)
D-Val-D-Thr-D-Leu-D-Lys-D-Cys-D-Asn-D-Pro-D-Ser-D-Ser-D-Lys-D-Lys-D-Phe-D-Val;
or (SEQ ID NO: 19)
D-Lys-Gly-D-Leu-D-Tyr-D-Val-D-Thr-D-Leu-D-Lys-Gly-D-Asn-D-Pro-D-Ser-D-Ala-D-Lys-D-Lys-D-Phe-D-Val-D-Arg-D-Thr-Gly-D-Lys-D-Glu-Gly-D-Met.

In some embodiments, disclosed herein are polypeptides selected from an amino acid sequence that is at least 50% (for example, at least 50%, at least 55%, at least 60%, at least 65%, at least 70%, at least 75%, at least 80%, at least 85%, at least 90%, at least 95%, or more) identical to a sequence selected from SEQ ID NO:14, SEQ ID NO:15, SEQ ID NO:16, SEQ ID NO:17, SEQ ID NO:18, or SEQ ID NO:19.

In some embodiments, the peptides disclosed herein are modified to make them more cell-permeable. In some embodiments, the peptides disclosed herein are conjugated/fused to a peptide sequence that improves cell permeability. In some embodiments, the peptides disclosed herein are conjugated to the amino acid sequence KIKKVKKKGRK-GGG (SEQ ID NO:20); however, any sequence that improves cell permeability can be used. Additional examples of peptides for use in improving cell permeability can be found, for example, in WO/2007/1371151, US20150307847, and US20100160209, each of which is incorporated herein by reference in its entirety.

In some embodiments, the retro-inverso peptides can be selected from:

(SEQ ID NO: 21)
Lys-Ile-Lys-Lys-Val-Lys-Lys-Lys-Gly-Arg-Lys-Gly-
Gly-Gly-D-Lys-Gly-D-Leu-D-Tyr-D-Val-D-Thr-D-Leu-D-
Lys-D-Cys-D-Asn-D-Pro-D-Ser-D-Ser-D-Lys-D-Lys-D-
Phe-D-Val-D-Arg-D-Thr-Gly-D-Pro-D-Lys-D-Glu-Gly-D-
Met;

(SEQ ID NO: 22)
Lys-Ile-Lys-Lys-Val-Lys-Lys-Lys-Gly-Arg-Lys-Gly-
Gly-Gly-Gly-D-Leu-D-Tyr-D-Val-D-Thr-D-Leu-D-Lys-D-
Cys-D-Asn-D-Pro-D-Ser-D-Ser-D-Lys-D-Lys;

(SEQ ID NO: 23)
Lys-Ile-Lys-Lys-Val-Lys-Lys-Lys-Gly-Arg-Lys-Gly-
Gly-Gly-D-Val-D-Thr-D-Leu-D-Lys-D-Cys-D-Asn-D-Pro-
D-Ser-D-Ser-D-Lys-D-Lys-D-Phe-D-Val-D-Arg-D-Thr;

(SEQ ID NO: 24)
Lys-Ile-Lys-Lys-Val-Lys-Lys-Lys-Gly-Arg-Lys-Gly-
Gly-Gly-Gly-D-Leu-D-Tyr-D-Val-D-Thr-D-Leu-D-Lys-D-
Cys-D-Asn-D-Pro-D-Ser-D-Ser-D-Lys-D-Lys-D-Phe-D-
Val;

(SEQ ID NO: 25)
Lys-Ile-Lys-Lys-Val-Lys-Lys-Lys-Gly-Arg-Lys-Gly-
Gly-Gly-D-Val-D-Thr-D-Leu-D-Lys-D-Cys-D-Asn-D-Pro-
D-Ser-D-Ser-D-Lys-D-Lys-D-Phe-D-Val;
or (SEQ ID NO: 26)
Lys-Ile-Lys-Lys-Val-Lys-Lys-Lys-Gly-Arg-Lys-Gly-
Gly-Gly-D-Lys-Gly-D-Leu-D-Tyr-D-Val-D-Thr-D-Leu-D-
Lys-Gly-D-Asn-D-Pro-D-Ser-D-Ala-D-Lys-D-Lys-D-Phe-
D-Val-D-Arg-D-Thr-Gly-D-Lys-D-Glu-Gly-D-Met.

In some embodiments, disclosed herein are polypeptides selected from an amino acid sequence that is at least 50% (for example, at least 50%, at least 55%, at least 60%, at least 65%, at least 70%, at least 75%, at least 80%, at least 85%, at least 90%, at least 95%, or more) identical to a sequence selected from SEQ ID NO:21, SEQ ID NO:22, SEQ ID NO:23, SEQ ID NO:24, SEQ ID NO:25, or SEQ ID NO:26.

In some embodiments, the peptides disclosed herein are conjugated to the sequence KIKKVKKKGRKGGG (SEQ ID NO:20); however, any sequence that improves cell permeability (cell penetration) can be used. In some embodiments, the peptides disclosed herein are conjugated to a sequence that is at least 50% (for example, at least 50%, at least 55%, at least 60%, at least 65%, at least 70%, at least 75%, at least 80%, at least 85%, at least 90%, at least 95%, or more) identical to KIKKVKKKGRKGGG (SEQ ID NO:20).

Compositions

Compositions, as described herein, comprising an active compound and an excipient of some sort may be useful in a variety of applications. For example, pharmaceutical compositions comprising an active compound and an excipient may be useful for the treatment or prevention of a cancer, or for the treatment or prevention of a neurodegenerative disease. The compositions can comprise any of the polypeptides (active compounds) disclosed herein and an excipient.

In one aspect, disclosed herein is a composition comprising a pharmaceutically acceptable carrier and an isolated polypeptide comprising an amino acid sequence set forth in SEQ ID NO:3.

In one embodiment, the polypeptide is linked to a second polypeptide, wherein the second polypeptide improves cell permeability of the polypeptide. In one embodiment, the composition further comprises an additional therapeutic agent.

In one aspect, disclosed herein is a composition comprising a pharmaceutically acceptable carrier and an isolated polypeptide comprising an amino acid sequence set forth in SEQ ID NO:4.

"Excipients" include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Exemplary excipients include, but are not limited to, any non-toxic, inert solid, semi-solid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on what the composition is useful for. For example, with a pharmaceutical composition or cosmetic composition, the choice of the excipient will depend on the route of administration, the agent being delivered, time course of delivery of the agent, etc., and can be administered to humans and/or to animals, orally, rectally, parenterally, intracisternally, intravaginally, intranasally, intraperitoneally, topically (as by powders, creams, ointments, or drops), buccally, or as an oral or nasal spray.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Additionally, the composition may further comprise a polymer. Exemplary polymers contemplated herein include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch, dextran, dextran derivatives, chitosan, and alginic acid and its various salts, carageenan, various gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polyglycolide, polyl(lactide-co-glycolide) and poly(.epsilon.-caprolactone-co-glycolide)-, carboxyvinyl polymers and their salts (e.g., carbomer), polyvinylpyrrolidone (PVP), polyacrylic acid and its salts, polyacrylamide, polyacilic acid/acrylamide copolymer, polyalkylene oxides such as polyethylene oxide, polypropylene oxide, poly(ethylene oxide-propylene oxide), and a Pluronic polymer, polyoxyethylene (polyethylene glycol), polyanhydrides, polyvinylalchol, polyethyleneamine and polypyrridine, polyethylene glycol (PEG) polymers, such as PEGylated lipids (e.g., PEG-stearate, 1,2-Di stearoyl-sn-glycero-3-Phosphoethanolamine-N-[Methoxy(Polyethylene glycol)-1000], 1,2-Distearoyl-sn-glycero-3-Phosphoethanolamine-N-[Methoxy(Polyethylene glycol)-2000], and 1,2-Di stearoyl-sn-glycero-3-Phosphoethanolamine-N-[Methoxy(Polyethylene glycol)-5000]), copolymers and salts thereof.

Additionally, the composition may further comprise an emulsifying agent. Exemplary emulsifying agents include, but are not limited to, a polyethylene glycol (PEG), a polypropylene glycol, a polyvinyl alcohol, a poly-N-vinyl pyrrolidone and copolymers thereof, poloxamer nonionic surfactants, neutral water-soluble polysaccharides (e.g., dextran, Ficoll, celluloses), non-cationic poly(meth)acrylates, non-cationic polyacrylates, such as poly(meth)acrylic acid, and esters amide and hydroxyalkyl amides thereof, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the emulsifying agent is cholesterol.

Liquid compositions include emulsions, microemulsions, solutions, suspensions, syrups, and elixirs. In addition to the active compound, the liquid composition may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable compositions, for example, injectable aqueous or oleaginous suspensions may be formulated according to the known art using suitable dispersing or wetting agents and suspending agents. The sterile injectable preparation may also be a injectable solution, suspension, or emulsion in a nontoxic parenterally acceptable diluent or solvent, for example, as a solution in 1,3-butanediol. Among the acceptable vehicles and solvents for pharmaceutical or cosmetic compositions that may be employed are water, Ringer's solution, U.S.P. and isotonic sodium chloride solution. In addition, sterile, fixed oils are conventionally employed as a solvent or suspending medium. Any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80. The injectable composition can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be in the form of suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid compositions include capsules, tablets, pills, powders, and granules. In such solid compositions, the particles are mixed with at least one excipient and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

Tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Compositions for topical or transdermal administration include ointments, pastes, creams, lotions, gels, powders, solutions, sprays, inhalants, or patches. The active compound is admixed with an excipient and any needed preservatives or buffers as may be required.

The ointments, pastes, creams, and gels may contain, in addition to the active compound, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the active compound, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the nanoparticles in a proper medium. Absorption enhancers can also be used to increase the flux of the compound across the skin. The rate can be controlled by either providing a rate controlling membrane or by dispersing the particles in a polymer matrix or gel.

The active ingredient may be administered in such amounts, time, and route deemed necessary in order to achieve the desired result. The exact amount of the active ingredient will vary from subject to subject, depending on the species, age, and general condition of the subject, the severity of the infection, the particular active ingredient, its mode of administration, its mode of activity, and the like. The active ingredient, whether the active compound itself, or the active compound in combination with an agent, is preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

The active ingredient may be administered by any route. In some embodiments, the active ingredient is administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, enteral, sublingual; by intratracheal instillation, bronchial instillation, and/or inhalation; and/or as an oral spray, nasal spray, and/or aerosol. In general, the most appropriate route of administration will depend upon a variety of factors including the nature of the active ingredient (e.g., its stability in the environment of the gastrointestinal tract), the condition of the subject (e.g., whether the subject is able to tolerate oral administration), etc.

The exact amount of an active ingredient required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

Methods of Treatment—Neurodegenerative Disease

In some embodiments, the polypeptides disclosed herein can act as inhibitors of JNK family kinases. These JNK inhibitors can prevent cell death and are therefore used in methods for the treatment of disorders associated with excessive death (for example, neurodegenerative diseases).

In one aspect, provided herein is a method of treating a neurodegenerative disease in a subject in need thereof, comprising administering to the subject a composition comprising a pharmaceutically acceptable carrier and an isolated polypeptide comprising an amino acid sequence set forth in SEQ ID NO:3.

In one embodiment, the neurodegenerative disease is selected from Alzheimer's disease, Parkinson's disease, or dyskinesia. In one embodiment, the neurodegenerative disease is Alzheimer's disease. In one embodiment, the neurodegenerative disease is Parkinson's disease.

In one embodiment, provided herein is a method of treating Alzheimer's disease in a subject in need thereof, comprising administering to the subject a composition comprising a pharmaceutically acceptable carrier and an isolated polypeptide comprising a pharmaceutically acceptable carrier and an isolated polypeptide comprising an amino acid sequence set forth in SEQ ID NO:3.

In one embodiment, provided herein is a method of treating Parkinson's disease in a subject in need thereof, comprising administering to the subject a composition comprising a pharmaceutically acceptable carrier and an isolated polypeptide comprising a pharmaceutically acceptable carrier and an isolated polypeptide comprising an amino acid sequence set forth in SEQ ID NO:3.

In one embodiment, provided herein is a method of treating dyskinesia in a subject in need thereof, comprising administering to the subject a composition comprising a pharmaceutically acceptable carrier and an isolated polypeptide comprising a pharmaceutically acceptable carrier and an isolated polypeptide comprising an amino acid sequence set forth in SEQ ID NO:3.

In one aspect, provided herein is a method of treating a neurodegenerative disease in a subject in need thereof, comprising administering to the subject a composition comprising a pharmaceutically acceptable carrier and an isolated polypeptide comprising an amino acid sequence selected from SEQ ID NO:3, SEQ ID NO:16, or SEQ ID NO:23.

In one embodiment, provided herein is a method of treating Alzheimer's disease in a subject in need thereof, comprising administering to the subject a composition comprising a pharmaceutically acceptable carrier and an isolated polypeptide comprising a pharmaceutically acceptable carrier and an isolated polypeptide comprising an amino acid sequence selected from SEQ ID NO:3, SEQ ID NO:16, or SEQ ID NO:23.

In one embodiment, provided herein is a method of treating Parkinson's disease in a subject in need thereof, comprising administering to the subject a composition comprising a pharmaceutically acceptable carrier and an isolated polypeptide comprising a pharmaceutically acceptable carrier and an isolated polypeptide comprising an amino acid sequence selected from SEQ ID NO:3, SEQ ID NO:16, or SEQ ID NO:23.

In one embodiment, provided herein is a method of treating dyskinesia in a subject in need thereof, comprising administering to the subject a composition comprising a pharmaceutically acceptable carrier and an isolated polypeptide comprising a pharmaceutically acceptable carrier and an isolated polypeptide comprising an amino acid sequence selected from SEQ ID NO:3, SEQ ID NO:16, or SEQ ID NO:23.

In some embodiments, the methods include administration of compounds and compositions disclosed herein through intranasal delivery of the peptides. This delivery method can be further tested in hemiparkinsonian mice with dyskinesia.

Disease resulting from increased cell death include, for example, neurodegenerative diseases in some embodiments, the neurodegenerative disease is selected from Alzheimer's disease, Parkinson's disease, or dyskinesia.

In some embodiments, the neurodegenerative disease is selected from Alzheimer's Disease (or early-onset AD); Senile dementia of the Alzheimer's type (or late onset AD); Parkinson's disease; Pick's Disease; Huntington's disease; multiple system atrophy (dementia combined with ataxia, Parkinson's disease, etc.); progressive supranuclear palsy; diffuse Lewy body disease; corticodentatonigral degeneration; hallervorden-Spatz disease; progressive familial myoclonic epilepsy; striatonigral degeneration; progressive supranuclear palsy; torsion dystonia; spasmodic torticollis and other restricted; dyskinesias; familial tremor; Gilles de la Tourette syndrome; Syndromes of progressive ataxia; Cerebellar cortical degeneration; Olivopontocerebellar atrophy; Friedrich's ataxia and related spinocerebellar degenerations; Shy-Drager syndrome; subacute necrotizing encephalopathy; motor neuron disease without sensory changes; amyotrophic lateral sclerosis; infantile spinal muscular atrophy; juvenile spinal muscular atrophy; other forms of familial spinal muscular atrophy; primary lateral sclerosis; hereditary spastic paraplegia; motor neuron disease with sensory changes; peroneal muscular atrophy; hypertrophic interstitial polyneuropathy; other forms of chronic progressive neuropathy; syndromes of progressive visual loss; or retinitis pigmentosa.

In certain embodiments, said disease resulting from increased cell death include is a traumatic brain injury. In certain embodiments, said traumatic brain injury is stroke.

Combination Therapies—Neurodegenerative Diseases

In some embodiments, the compounds or compositions described herein can be combined with an additional therapeutic agent. In some embodiments, the additional therapeutic agent is selected from Alzheimer's disease medications such as memantine, donepezil (Aricept®), galantamine (Reminyl®), tacrine hydrochloride (Cognex®), and rivastigmine tartrate (Exelon®). Donepezil ([(R,S)-1-benzyl-4-[(5,6-dimethoxy-1-indanon)-2-yl]-methylpiperidine hydrochloride], also known as Aricept®) is a reversible, noncompetitive, piperidine-type acetylcholinesterase inhibitor. Studies have shown that daily administration of donepezil (5 and 10 mg/day) can lead to significantly improved cognition and global clinical function compared with placebo in short and long-term trials. Donepezil is described, for example, in U.S. Pat. Nos. 6,372,760; 6,245,911; 6,140,321; 5,985,864; and 4,895,841, all of which are incorporated herein by reference in their entireties. Memantine (1-amino-3,5-dimethyl adamantane) is described, for example, in U.S. Pat. Nos. 4,122,193; 4,273,774; 5,061,703, all of which are incorporated herein by reference in their entireties. Memantine is an Alzheimer's disease medication acting on the glutamatergic system by blocking NMDA glutamate receptors. Memantine is advantageous because it lacks the side effects of other NMDA receptor antagonists at similar therapeutic doses.

In some embodiments, the additional therapeutic agent is selected from Parkinson's disease medications such as opioid antagonists (e.g. naloxone) and agonists (e.g. morphine), alpha-2 adrenoceptor antagonists (idozoxan, fipamezole), 5-HT1 a receptor agonists (sarizotan), 5-HT2a/c receptor antagonists (quetiapine), cannabinoid receptor agonists (e.g. nabilone), magnesium sulphate, 3,4-methylenedioxymethamphetamine (ecstasy), nicotine and the anti-convulsant, levatiracetam. However, none of these treatments have been effective or useful in late stage clinical trials.

The inventors also surprisingly found that suppression of JNK activity in the striatum alleviates dyskinesia, a devastating side effect of the most common anti-parkinsonian therapy with dopamine precursor L-DOPA. The dominant-negative peptides can be effective anti-dyskinetic therapy. At present, there are no effective anti-dyskinetic therapies.

Methods of Treatment—Cancer

In some embodiments, the polypeptides disclosed herein can act as activators of JNK family kinases. These INK activators can suppress cell proliferation and/or can induce cell death. These properties allow JNK activators disclosed herein to be used against disorders associated with excessive proliferation, for example, a cancer.

In one aspect, disclosed herein is a method of treating a cancer in a subject in need thereof, comprising administering to the subject a composition comprising a pharmaceutically acceptable carrier and an isolated polypeptide comprising an amino acid sequence set forth in SEQ ID NO:4.

In one aspect, disclosed herein is a method of treating a cancer in a subject in need thereof, comprising administering to the subject a composition comprising a pharmaceutically acceptable carrier and an isolated polypeptide comprising an amino acid sequence selected from SEQ ID NO:4, SEQ ID NO:17, or SEQ ID NO:24.

In some embodiments, the methods described herein are used for the treatment of the prevention of a cancer, for example, melanoma, lung cancer (including lung adenocarcinoma, basal cell carcinoma, squamous cell carcinoma, large cell carcinoma, bronchioloalveolar carcinoma, bronchogenic carcinoma, non-small-cell carcinoma, small cell carcinoma, mesothelioma); breast cancer (including triple negative breast cancer (TNBC), ductal carcinoma, lobular carcinoma, inflammatory breast cancer, clear cell carcinoma, mucinous carcinoma, serosal cavities breast carcinoma); colorectal cancer (colon cancer, rectal cancer, colorectal adenocarcinoma); anal cancer; pancreatic cancer (including pancreatic adenocarcinoma, islet cell carcinoma, neuroendocrine tumors); prostate cancer; prostate adenocarcinoma; ovarian carcinoma (ovarian epithelial carcinoma or surface epithelial-stromal tumor including serous tumor, endometrioid tumor and mucinous cystadenocarcinoma, sex-cord-stromal tumor); liver and bile duct carcinoma (including hepatocellular carcinoma, cholangiocarcinoma, hemangioma); esophageal carcinoma (including esophageal adenocarcinoma and squamous cell carcinoma); oral and oropharyngeal squamous cell carcinoma; salivary gland adenoid cystic carcinoma; bladder cancer; bladder carcinoma; carcinoma of the uterus (including endometrial adenocarcinoma, ocular, uterine papillary serous carcinoma, uterine clear-cell carcinoma, uterine sarcomas, leiomyosarcomas, mixed mullerian tumors); glioma, glioblastoma, medulloblastoma, and other tumors of the brain; kidney cancers (including renal cell carcinoma, clear cell carcinoma, Wilm's tumor); cancer of the head and neck (including squamous cell carcinomas); cancer of the stomach (gastric cancers, stomach adenocarcinoma, gastrointestinal stromal tumor); testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumor, lipoma, angiolipoma, granular cell tumor, neurofibroma, schwannoma, angiosarcoma, liposarcoma, rhabdomyosarcoma, osteosarcoma, leiomyoma, leiomysarcoma, skin, including melanoma, cervical, retinoblastoma, head and neck cancer, pancreatic, brain, thyroid, testicular, renal, bladder, soft tissue, adenal gland, urethra, cancers of the penis, myxosarcoma, chondrosarcoma, osteosarcoma, chordoma, malignant fibrous histiocytoma, lymphangiosarcoma, mesothelioma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, Islet cell carcinoma, malignant carcinoid, malignant paraganglioma, melanoma, Merkel cell neoplasm, cystosarcoma phylloide, salivary cancers, thymic carcinomas, and cancers of the vagina among others.

Combination Therapies—Additional Chemotherapeutic Agents

In one embodiment, a compound or composition disclosed herein can be administered in combination with an additional chemotherapeutic agent. In one embodiment, disclosed herein is a composition comprising a polypeptide comprising an amino acid sequence set forth in SEQ ID NO:4 and an additional chemotherapeutic agent.

Additional chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antis, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, $E.\ coli$ L-asparaginase, emetine, epoetin-α, $Erwinia$ L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Additional chemotherapeutic agents or therapeutic agents that can be administered in combination with the compounds disclosed herein can include bevacizumab, sutinib, sorafenib, 2-methoxyestradiol, finasunate, vatalanib, vandetanib, aflibercept, volociximab, etaracizumab, cilengitide, erlotinib, cetuximab, panitumumab, gefitinib, trastuzumab, atacicept, rituximab, alemtuzumab, aldesleukine, atlizumab, tocilizumab, temsirolimus, everolimus, lucatumumab, dacetuzumab, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, oblimersen, plitidepsin, talmapimod, enzastaurin, tipifarnib, perifosine, imatinib, dasatinib, lenalidomide, thalidomide, simvastatin, and celecoxib.

EXAMPLES

The following examples are set forth below to illustrate the compounds, peptides, compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Peptide Mini-Scaffold Facilitates JNK3 Activation in Cells

Three-kinase mitogen-activated protein kinase (MAPK) signaling cascades are present in virtually all eukaryotic cells. MAPK cascades are organized by scaffold proteins, which assemble cognate kinases into productive signaling complexes. Arrestin-3 facilitates JNK activation in cells, and a short 25-residue arrestin-3 peptide was identified as the critical JNK3-binding element. In this example, it is demonstrated that this peptide also binds MKK4, MKK7, and ASK1, which are upstream JNK3-activating kinases. This peptide is sufficient to enhance JNK3 activity in cells. A homologous arrestin-2 peptide, which differs only in four positions, binds MKK4, but not MKK7 or JNK3, and is ineffective in cells at enhancing activation of JNK3. This peptide or its mimics can regulate MAPKs, affecting cellular decisions to live or die.

The spatial and temporal organization of proteins within a cell is critical for coordinating essential activities[1]. Appropriate cellular response to external or internal stimuli often requires precise orchestration by scaffold proteins, which determine the specificity and precise time course of signaling. In particular, the specificity of signal transduction through mitogen activated protein kinase (MAPK) cascades is highly dependent on scaffold proteins[2-4]. MAPK signaling is involved in the regulation of key cellular behaviors, from proliferation to differentiation and apoptotic death[4]. The overall architecture of three-kinase MAPK cascades is conserved from yeast to mammals[5]. Most cells have multiple MAPKs, MAPK kinases (MAPKKs), and MAPKK kinases (MAPKKKs), so signaling outcome is often determined by scaffolds organizing particular MAPKKK-MAPKK-MAPK complexes[2-4,6].

The c-Jun NH$_2$-terminal protein kinases (JNKs) belong to the MAPK family. JNKs regulate normal physiological processes of cell proliferation, apoptosis, differentiation, and migration[7]. JNKs were also implicated in many diseases, from cancer to neurological and immunological disorders[8-10]. Full activation of all JNKs requires double phosphorylation of the T-X-Y motif in the activation loop by two upstream kinases, MKK4 (tyrosine) and MKK7 (threonine)[11]. Similar to other MAPKs, JNK activation is dependent on scaffolding proteins, such as JIPs[12]. Arrestins, which specifically bind active phosphorylated G protein-coupled receptors (GPCRs), were first discovered as negative regulators of GPCR signaling via G proteins[13,14]. Among the four arrestin subtypes expressed in vertebrates[15], only arrestin-3 proteins promotes the activation of JNK3[16], as well as ubiquitous JNK1/2[17] in cells, acting as a scaffold that brings together MAPKKK ASK1[16,18] MAPKKs MKK4[16,18,19] and MKK7[17,20], and several isoforms of JNK1/2/3[16-18,21,22]. Recently, the first 25 residues of arrestin-3 was identified as the key JNK3 binding site[23]. It is demonstrated in this example that this short arrestin-3-derived peptide also binds ASK1 and MKK4/7 and facilitates JNK3 activation in intact cells.

Results

It was recently found that while three elements in both arrestin-3 domains are involved in JNK3 binding, the peptide representing the first 25 residues of arrestin-3 (T1A) is the key interaction site[23]. This opens up three possibilities. First, if T1A only binds JNK3, but not the other kinases in the cascade, it could recruit JNK3 away from functional scaffolds, thereby suppressing JNK3 activation. Second, if T1A binds several kinases in the JNK3 activation module, but does not promote JNK3 phosphorylation, it might act as a dominant-negative silent scaffold, similar to arrestin-3-KNC mutants[24]. Finally, if T1A binds the same kinases as arrestin-3 and facilitates the signaling in the JNK3 cascade, it would be the smallest active MAPK scaffold known, which opens new avenues for the manipulation of MAPK signaling in cells for research and therapeutic purposes.

T1A was expressed in *E. coli* as an MBP-fusion and purified it on an amylose column[23]. The ability of purified GST-MKK4 or GST-MKK7 (FIG. 1A) to bind MBP-T1A immobilized on an amylose column was tested in an in vitro pull-down assay, where MBP and MBP-arrestin-3 served as negative and positive controls, respectively (FIG. 1B). MBP-T1A, but not control MBP, effectively retained both kinases (FIG. 1B). Interestingly, similar to full-length arrestin-3, T1A peptide demonstrated stronger interaction with MKK4 than with MKK7 (FIG. 1B, lower panel). Thus, in addition to JNK3[23], T1A peptide binds both MKKs known to phosphorylate it. Since the pull-down was performed with purified proteins, the data prove that the interactions of T1A with MKK4 and MKK7 are direct and do not involve any intermediaries or helpers. Next, it was tested whether T1A binds the uppermost kinase in the cascade, ASK1. Because ASK1 is not available in purified form, HA-tagged ASK1 and YFP-tagged T1A (using YFP as a control) were co-expressed in COS7 cells, lysed the cells, and immunoprecipitated YFP constructs with anti-GFP antibody (FIG. 1C). It was found that HA-ASK1 was effectively co-immunoprecipitated with YFP-T1A, but not with control YFP (FIG. 1C). Thus, in addition to JNK3[23], T1A peptide binds all upstream kinases of its activation cascade, ASK1, MKK4, and MKK7 (FIG. 1).

Figure 2:
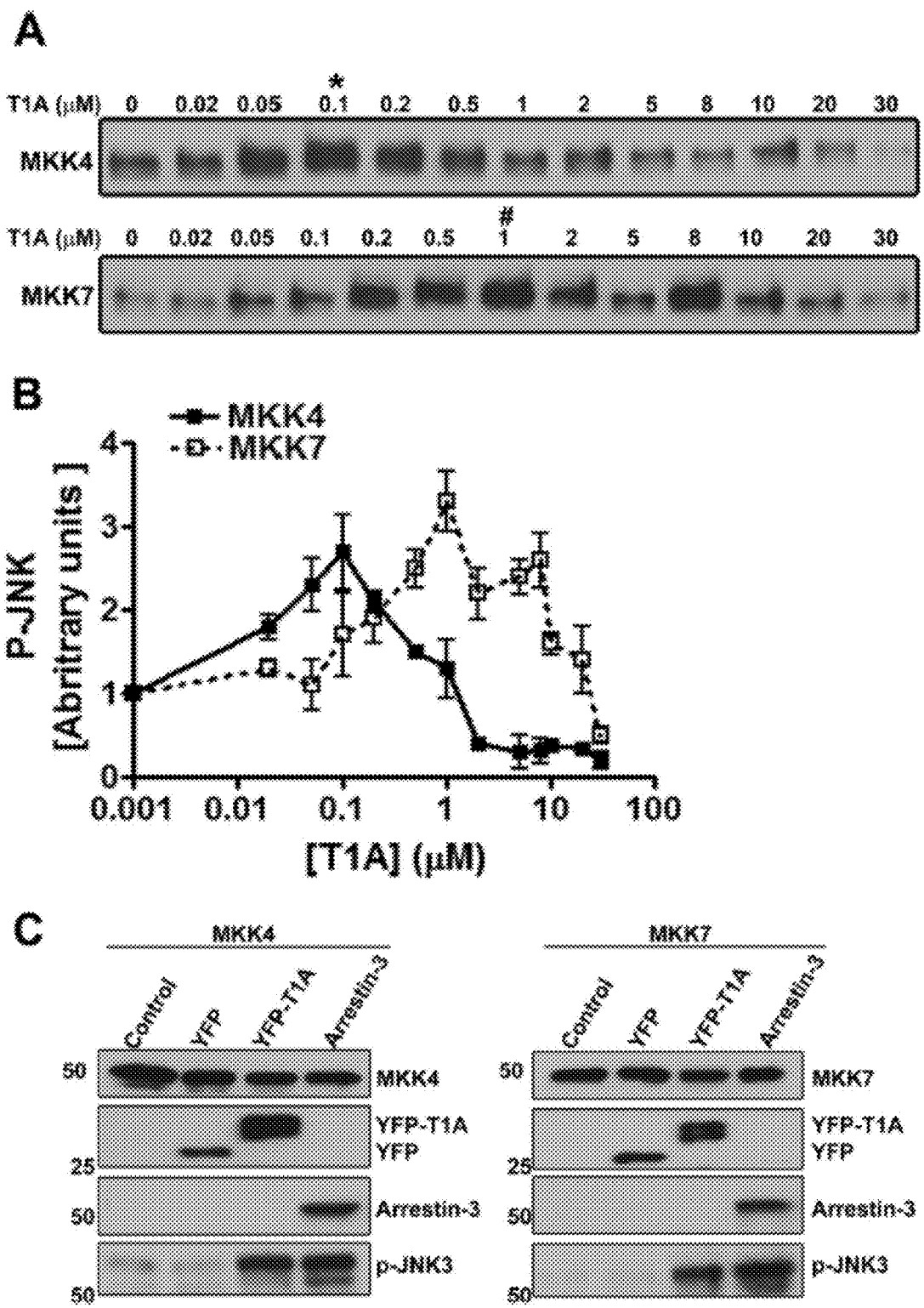
FIG. 2. T1A facilitates JNK3 phosphorylation by MKK4 and MKK7. a) Representative autoradiograms showing JNK3α2 phosphorylated by purified MKK4 (upper panel) and MKK7 (lower panel) at the indicated concentration of synthetic purified T1A peptide (10-s incubation). b) Quantification of JNK3α2 phosphorylation by MKK4 and MKK7. c) JNK3α2 phosphorylation by MKK4 and MKK7 in HEK293 cells co-expressing JNK3α2 with MKK4 or MKK7 (control) and YFP, YFP-T1A, or arrestin-3.

Next, it was tested whether T1A acts as a scaffold facilitating signaling. To this end, experiments used purified proteins, because they provide the most definitive data supporting a direct interaction. As purified ASK1 is not available, MKK4-JNK3 and MKK7-JNK3 modules were reconstituted in the absence and presence of varying concentrations of synthetic purified T1A peptide and measured JNK3 phosphorylation (FIG. 2A). In both cases bell-shaped curves were obtained reflecting JNK3 phosphorylation level as a function of T1A concentration (FIG. 2B). This dependence, where signaling is increased at lower scaffold concentrations and decreased at higher, was also found for scaffolding of these modules by full-length arrestin-3[20]. It is believed to be a characteristic of simple scaffolds, which act by bringing the enzyme and substrate together, as lower scaffold concentrations make the formation of complete scaffold-enzyme-substrate ternary complexes likely, whereas higher concentrations increase the probability of formation of incomplete enzyme-scaffold and substrate-scaffold binary complexes, suppressing the signaling[25,26]. The optimal concentration of a scaffolding protein for signaling depends on its affinity for the proteins it scaffolds[20,25,26].

Previous work suggested that the efficiency of JNK3 phosphorylation in the complex that includes MKK4 and arrestin-3 is higher than the efficiency of JNK3 phosphorylation by MKK4 in the absence of arrestin-3[20]. Since these experiments were performed with pure components, the data show that simultaneous direct binding to T1A of MKK4/7 (FIG. 1A) and their substrate JNK3[23] places MKKs into a favorable position to phosphorylate JNK3 (FIG. 2A,B). Previously it was found that the optimal concentrations of arrestin-3 for scaffolding MKK4-JNK3 and MKK7-JNK3 modules are ~0.6 µM and ~6 µM[20], reflecting lower affinity of arrestin-3 for MKK7 than for MKK4[20]. Interestingly, the optimal concentration of T1A for promoting JNK3 phosphorylation by MKK4 is lower than for MKK7-JNK3 module (FIG. 2B), in line with more avid binding of this peptide to MKK4 (FIG. 1B). Intriguingly, in both cases optimal T1A concentrations were ~10-times lower than those of full-length arrestin-3. These results suggest that T1A has higher affinity for MKKs and/or JNK3, in line with its ability to retain more MKKs than arrestin-3 (FIG. 1B). This phenomenon might be explained by greater accessibility of T1A peptide when it is free and not in the context of full-length arrestin-3, where it is partially shielded by other elements of the N-domain[27].

To test whether T1A can promote JNK3 phosphorylation by MKKs in cells, MKK4 or MKK7 was co-expressed with YFP-T1A in COS7 cells, using YFP and full-length arrestin-3 as negative and positive controls, respectively (FIG. 2C). It was found that YFP-T1A, but not YFP, increases JNK3 phosphorylation by both MKKs, similar to arrestin-3. Thus, T1A is necessary and sufficient to promote the signaling in MKK4/7-JNK3 modules both in vitro and in intact cells.

Figure 3:
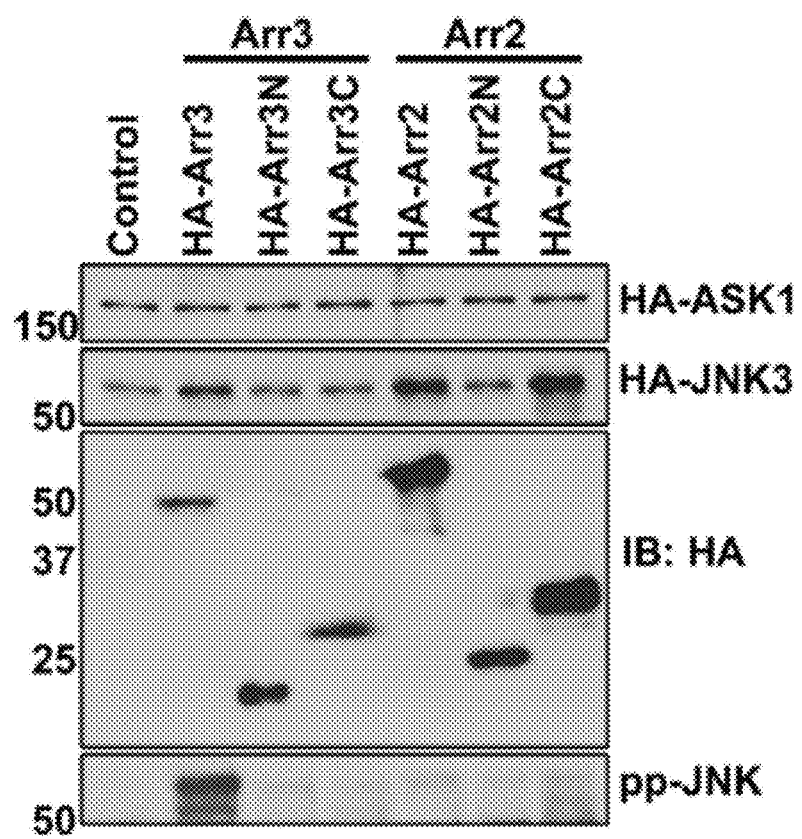
FIG. 3. Separated arrestin domains do not promote JNK activation. Western blot of lysates of HEK293 cells co-expressing HA-ASK1 and HA-JNK3α2 (Control), or with HA-tagged full-length arrestin-3 (Arr3), arrestin-2 (Arr2), or separated N- and C-domains of the two non-visual arrestins (Arr3N, Arr2N, Arr3C, Arr2C). Phospho-JNK blot shows that among these constructs only full-length arrestin-3 facilitates JNK3α2 phosphorylation in cells.

T1A constitutes a small part of the arrestin-3 N-domain[27]. All arrestins consist of two domains[27-30], which fold independently, can be expressed separately, and retain certain functions[18,31,32]. Therefore, tests were performed as to whether separated domains of arrestin-3, as well as the other ubiquitously expressed non-visual subtype, arrestin-2, which also binds kinases of the JNK3 activation cascade[18], can promote JNK3 phosphorylation in cells. To this end, both arrestins and their individual domains with the same HA-tag were expressed in COS7 cells (to compare their expression on the same blot) along with ASK1 and JNK3 (FIG. 3). It was confirmed that arrestin-3 expression significantly increases JNK3 phosphorylation in cells, whereas arrestin-2 does not[16,18,33] and found no effect of the separated domains of either arrestin (FIG. 3).

Figure 4:
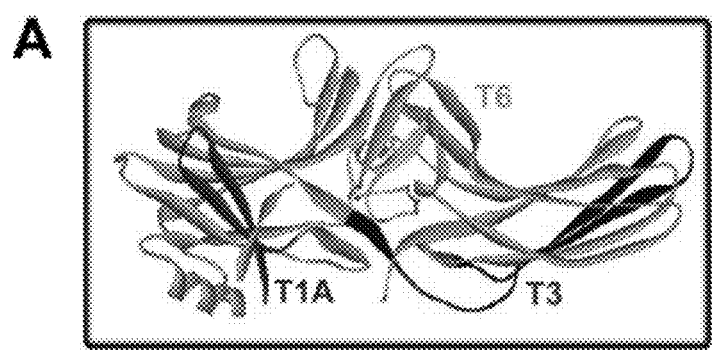
FIG. 4. T1A facilitates JNK3 activation in cells. a) The structure of arrestin-3 (PDB: 3P2D;[27]) with the three peptides implicated in JNK3 binding[23] shown in red (T1A), blue (T3), and green (T6). b) HEK293 cells co-expressed HA-ASK1 and HA-JNK3α2 without (Control) or with full-length arrestin-3 (Arr3), YFP, or indicated YFP-tagged JNK3-binding peptides. The upper three blots show expression levels of indicated proteins; the lower blot shows that T1A facilitates JNK3α2 phosphorylation more efficiently than full-length arrestin-3. c) HEK293 cells co-expressed HA-ASK1 and HA-JNK3α2 with YFP (Control) or different concentrations of YFP-T1A. The upper two blots show expression levels of indicated proteins; the lower blot shows biphasic dependence of JNK3α2 phosphorylation on T1A level.
Figure 4:
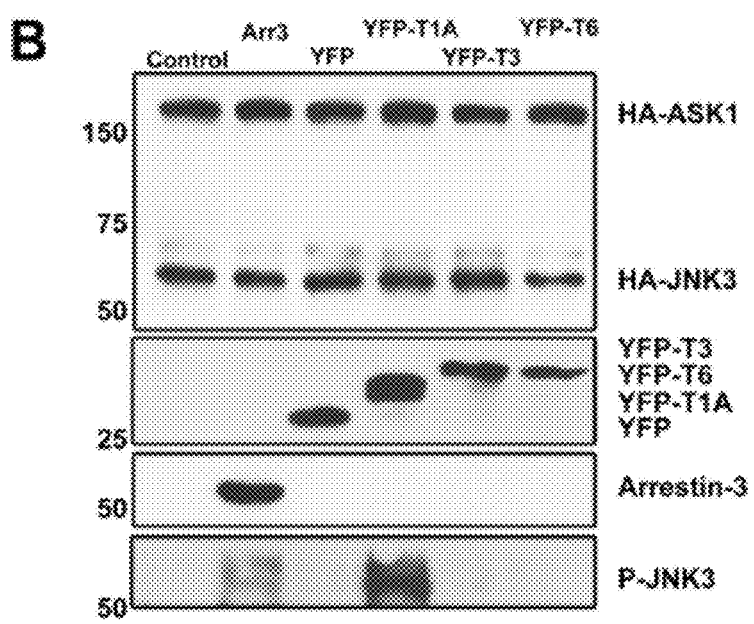
Figure 4:
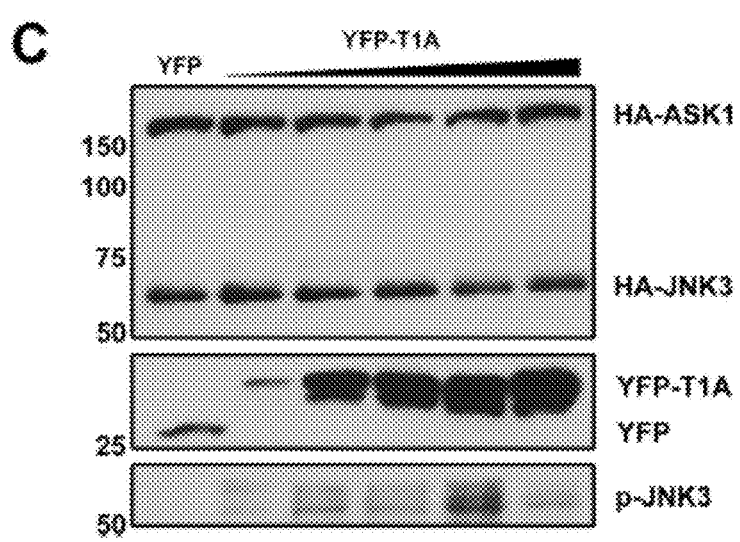

T1A effectively enhanced JNK3 phosphorylation by MKK4 and MKK7 (FIGS. 1,2), whereas full-length arrestin-3 facilitates JNK3 phosphorylation upon co-expression with ASK1[16,18,21,33] which phosphorylates and activates MKKs. If the arrestin-3 N-domain fails to promote the activation of JNK3 because it can only scaffold MKK4/7-JNK3 modules, then the T1A peptide, which constitutes only a part of the arrestin-3 N-domain, would not be expected to promote JNK3 phosphorylation in the presence of ASK1 in cells. To test this, YFP fusions of T1A and two other JNK3-binding peptides T3 and T6 (FIG. 4A)[23] were co-expressed with JNK3 and ASK1 in COS7 cells and monitored JNK3 phosphorylation, using YFP and arrestin-3 as negative and positive controls, respectively (FIG. 4B). Arrestin-3 increased the level of JNK3 phosphorylation (FIG. 4B). T1A, but not other peptides, was also active, and the effect of T1A was greater than that of full-length arrestin-3 (FIG. 4B). To test whether T1A still functions as a simple scaffold in intact cells in the presence of overexpressed ASK1, as in the case of MKK4/7-JNK3 signaling modules (FIG. 2), ASK1 and JNK3 were co-expressed with YFP (control) and varying amounts of YFP-T1A (FIG. 4C). The dose-response curve for T1A in these experiments was also biphasic, with a clear optimum, indicating that T1A is a simple scaffold of the three-kinase cascade, similar to full-length arrestin-3[19].

Figure 5:
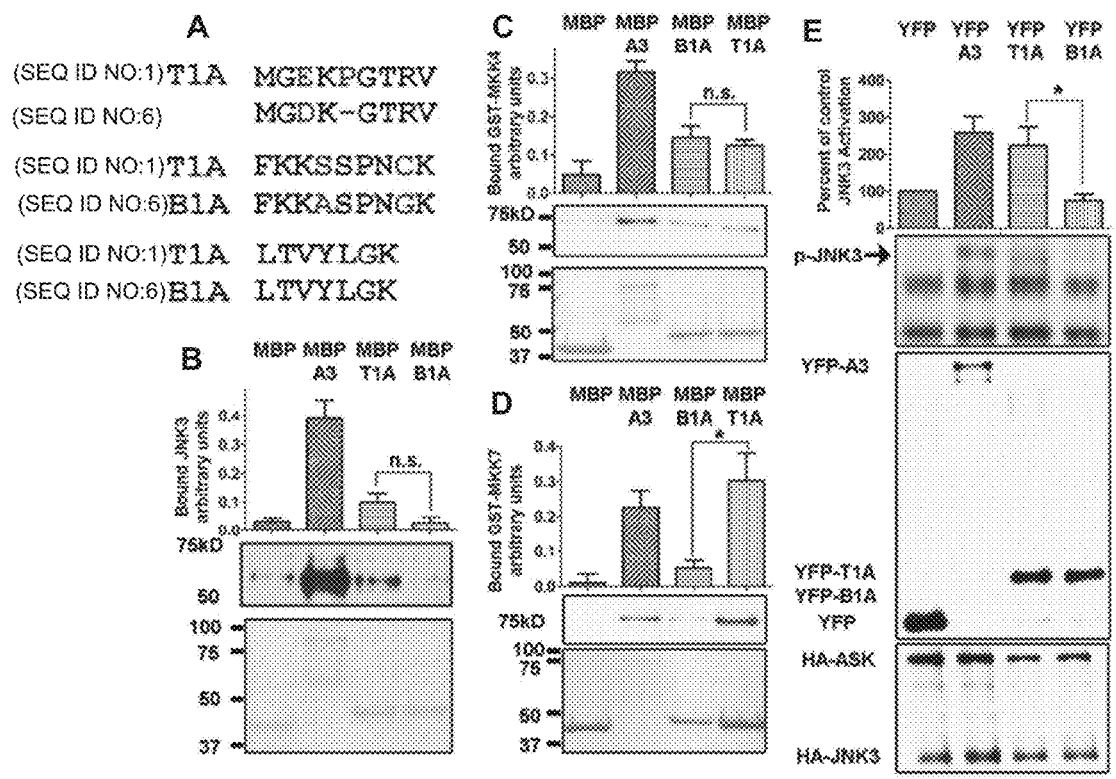
FIG. 5. T1A activity is specific. a) Sequence comparison of arrestin-3-derived T1A and B1A, derived from arrestin-2, which does not facilitate JNK3 activation. Residues that differ between T1A and B1A are shown in magenta. b, c, d) Pull-down of purified JNK3 (b), MKK4 (c), and MKK7 (d) by MBP (negative control), MBP-arrestin-3 (positive control), MBP-T1A, and MBP-B1A, was performed, as described in Methods. Lower panels, Coomassie gels of loaded MBP-fusions; middle panels, Western blots of retained JNK3 (b), MKK4 (c), and MKK7 (d); upper panels, quantification of Western blots from 3-4 independent experiments. Note that B1A binds MKK4 like T1A, but does not appreciably interact with JNK3 or MKK7. e) HEK293 cells co-expressed HA-ASK1 and HA-JNK3α2 with YFP (negative control), YFP-arrestin-3 (Arr3, positive control), YFP-T1A, or YFP-B1A. Lower two blots show expression levels of indicated proteins; upper blot and bar graph (quantification of JNK3α2 phosphorylation in four independent experiments) show that T1A facilitates JNK3α2 phosphorylation, whereas B1A does not. *, $p<0.05$; n.s., not significant. T1A sequence shown is SEQ ID NO:1. B1A sequence shown is SEQ ID NO:6.

To test the specificity of T1A action, its ability to bind purified MKK4, MKK7, and JNK3 was compared with that of B1A, a homologous N-terminal peptide from closely related arrestin-2, which differs from T1A only in four positions (FIG. 5). B1A was chosen as a "natural" negative control, because arrestin-2, despite 78% sequence identity to arrestin-3[34], does not promote JNK3 activation in cells[16,18,21]. It was found that while both peptides comparably bind MKK4, B1A demonstrates less robust interaction with JNK3 and its other upstream activator, MKK7 (FIG. 5). To test whether this difference in binding translates into differential activity in cells, the ability of YFP-T1A and YFP-B1A to facilitate JNK3 activation were compared in cells over-expressing ASK1, using YFP-arrestin-3 and YFP as positive and negative controls, respectively. It was found that in contrast to T1A, arrestin-2-derived B1A does not function as a scaffold of ASK1-MKK4/7-JNK3 cascade in cells (FIG. 5e), indicating that specific sequence, rather than simple accessibility of this part of arrestins, determines its functional capabilities.

Thus, the first 25 residues contained in the T1A peptide are primarily responsible for the ability of arrestin-3 to scaffold the ASK1-MKK4/7-JNK3 signaling module. The lack of the activity of the arrestin-3 N-domain (FIG. 3), which contains the T1A peptide, along with facilitation of JNK3 phosphorylation in exactly the same experimental paradigm by T1A (FIG. 4), clearly indicates that when separated, this peptide is a lot more accessible than in the context of arrestin-3 or its N-domain. It is tempting to speculate that receptor binding of arrestin-3 stimulates its ability to promote JNK3 activation[16] by increasing the accessibility of the T1A element to relevant kinases. Significant flexibility of receptor-bound arrestins revealed by biophysical methods[35,36] supports this idea. While the crystal structure of arrestin-3 in complex with any GPCR is not available, the only existing structure of the arrestin-receptor complex, that of visual arrestin-1 bound to rhodopsin[37], is consistent with this hypothesis. Arrestin-3 elements that promote signaling leading to the activation of other MAPKs, such as ERK1/2[38] and p38[39], also need to be identified. The activation of these two kinases is strictly dependent on arrestin binding to the receptor[38,39], suggesting that arrestin elements that change conformation and/or become more exposed upon GPCR interaction are likely the prime suspects.

These data identify a relatively short arrestin-3-derived peptide as an effective scaffold of the ASK1-MKK4/7-JNK3 signaling cascade. However, T1A can be large enough to bind all the kinases involved simultaneously. Each residue has a structure —NH—CH(R)—CO—, with each bond >1.4 A. Thus, taking into account angles, a single reside has a length of ~3 A. Therefore, a 25-residue peptide in fully extended conformation can achieve a length of up to ~75 A, which is similar to the maximum "wingspan" (the distance between the far tips of the two arrestin domains) of all arrestins[27-30]. Nonetheless, limited size of T1A shows that peptides and/or non-peptide small molecule mimics can be used as tools to manipulate MAPK signaling for research and therapy. Many human disorders are caused by excessive cell proliferation (e.g., cancer) or death (e.g., Alzheimer's, Parkinson's, and other neurodegenerative diseases). Targeted activation of JNK family kinases usually has antiproliferative effect, whereas the activation of ERK1/2 promotes cell survival. Scaffolds facilitating signaling in these pathways can be easier to dose than direct pharmacological activators, making them safer intervention tools.

Methods and Materials

All restriction and DNA modifying enzymes (T4 DNA ligase, Vent DNA polymerase, and calf intestine alkaline phosphatase) were from New England Biolabs (Ipswich, Mass.). Other chemicals were from sources recently described[17,23].

Terminology

The systematic names of arrestin proteins were used: arrestin-1 (historic names S-antigen, 48 kDa protein, visual or rod arrestin), arrestin-2 (□-arrestin or □-arresting arrestin-3 (□-arrestin2 or hTHY-ARRX), and arrestin-4 (cone or X-arrestin; for unclear reasons its gene is called "arrestin 3" in the HUGO database).

MBP-Fusion Protein Constructs in pMal and MBP Pull-Down

To make MBP-fusions containing arrestin-2/3 elements, the cDNAs encoding arrestin fragments were subcloned into pMal-p2T (generous gift from Dr. Keiji Tanaka, Tokyo Institute of Medical Science) between Eco RI and Xho I sites in frame with MBP, as described[23]. MBP-Arr3 (full-length arrestin-3) was created by subcloning the corresponding cDNA into pMal-p2T between Eco RI and Not I sites[23]. All MBP-arrestin-3 fusion proteins contained the same TLVPRGSPGF (SEQ ID NO:29) linker between MBP and arrestin-3 or its fragments. The MBP protein used as negative control was purified using empty pMal-p2T vector containing the same linker with 10 additional residues: PGRLERPHRD (SEQ ID NO:30). MBP fusions were purified, as described[23]. MBP pull-down was performed, as described[23]. Briefly, Indicated MBP fusions (10-30 μg in 50 μL 20 mM Tris/150 mM NaCl) were immobilized on amylose resin (25 μL, 50% slurry, New England Biolabs) for 1 h at 4° C. with slight rotation. Purified, as described[40], MKK4/7 (10 μg in 50 μL 20 mM Tris/150 mM NaCl) were added to the immobilized MBP fusions and rotated gently for 2 h at 4° C. Samples were transferred to centrifuge filters (Durapore®-PVDF-0.65 μm), washed three times with 50 mM HEPES-Na, pH 7.3, 150 mM NaCl. The proteins were eluted by 100 μl of elution buffer (wash buffer containing 50 mM maltose) by gentle rotation for 5 min at 4° C. Eluates were analyzed by SDS-PAGE and Western blotting.

Kinase Purification and In Vitro Phosphorylation Assay

JNK3α2[20,23], and MKK4 and MKK7[17,20] were expressed in E. coli and purified as previously described[40]. The effect of arrestin-3 and MBP-T1A on the phosphorylation of JNK3α2 by MKK7 or MKK4 was analyzed by an in vitro kinase assay, as described[19,20]. Briefly, the assays were conducted in 10 μL containing the following final concentrations: 50 nM active MKK7 or MKK4, 1 μM JNK3α2, and indicated concentrations of arrestin-3 or T1A. The mixtures were incubated individually at 30° C. for 10 sec. The reactions were stopped by the addition of 15 μL of Laemmli SDS sample buffer (Sigma) and 2 μl of total reaction sample was subjected to SDS-PAGE (8%) and transferred polyvinylidene difluoride (PVDF) membranes (Millipore, Bedford, Mass.). Phosphorylated JNK3α2 was visualized by rabbit anti-phospho JNK antibody (Cell Signaling) and the level of JNK phosphorylation was quantified.

Peptide Synthesis

The T1A peptide (MGEKPGTRVFKKSSPNCKLTVYL-GK)(SEQ ID NO:1), representing the first 25 residues of arrestin-3, was synthesized using automated synthesis robot (Syrol, MultiSyntech, Witten, Germany) on NovaSyn® TGR R resin (13.5 μmol, Novabiochem, Darmstadt, Germany) with a fluorenylmethyloxycarbonyl chloride (FMOC)/tert-butyl strategy, as described[41]. FMOC-amino acids were from Iris Biotech and Novabiochem (Marktredwitz, Germany). Amino acid side chain protecting groups were used as following: trityl (Trt) for Asn and Cys; tBu for Glu, Thr, Ser and Tyr; tert-butyloxycarbonyl (Boc) for Lys; and pentamethyl-2,3-dihydrobenzofuran-5-sufonyl (Pbf) for Arg. Automated FMOC deprotection was carried out with 40% (v/v) piperidine (Sigma-Aldrich, Taufkirchen, Germany) in N,N-dimethylformamide (DMF; Biosolve, Valkenswaard, The Netherlands) for 3 min and 20% (v/v) piperidine in DMF for 10 min. The coupling of the amino acids was carried out twice. FMOC-amino acids were pre-incubated with OxymaPure (Iris Biotech) for 2 min. Following the addition of N,N'-diisopropylcarbodiimide (DIC; Iris Biotech), reaction was incubated for 40 min. After successful synthesis, peptides were cleaved from the resin with 90% trifluoroacetic acid (TFA) and 10% 1,2-ethanedithiol/thioanisole (v/v 3:7). Methionines were reduced with 1,2-ethanedithiol and trimethylsilyl bromide in TFA. Subsequently, peptides were purified on a reversed-phase C18 column (Phenomenex Jupiter 10u Proteo 90 Å: 250×21.2 mm; 7.8 μm; 90 Å) and analyzed by MALDI-TOF mass spectrometry (UltraflexII, Bruker, Bremen, Germany) and analytical reversed-phase HPLC on columns Phenomenex Kinetex 5u XB-C18 100 Å (Phenomenex: 250×4.6 mm; 5 μm; 100 Å) and Phenomenex Jupiter 4u Proteo 90 Å (Phenomenex: 250×4.6 mm; 4 μm; 90 Å). Eluent A was 0.1% TFA in $H_2O$ and eluent B 0.08% TFA in ACN. On both columns, a gradient of 10% eluent B in A to 60% eluent B in A in 40 min was used. Following this procedure, the peptide was ≥95% pure (theoretical $M_r$=2766.5 Da, experimental ([M+H]$^+$) =2767.6).

Plasmids, Cell Culture, and Transient Transfection

HA-tagged arrestins and their separated domains were constructed, as described[31]. Full-length arrestin-3 and its fragments with N-terminal YFP tag were constructed by subcloning the cDNA encoding YFP-arrestin-3 or YFP-tagged arrestin-3 fragments cDNAs into pcDNA3.1 between Eco RI and Hind III restriction sites.

COS-7 African green monkey cells were maintained in DMEM supplemented with 10% heat-inactivated FBS (Invitrogen), penicillin, and streptomycin at 37° C. in a humidified incubator with 5% $CO_2$. The cells were plated at 80-90% confluence and transfected using Lipofectamine 2000 (Invitrogen) according to the manufacturer's instructions. Cells were used 48 h post-transfection and serum-starved overnight before experiments.

Western Blotting and Measurement of JNK Phosphorylation in Intact Cells

COS-7 cells were incubated with phosphatase inhibitors (50 mM NaF and 10 mM $Na_3VO_4$) in serum-free medium for 15 min at 37° C.; washed with cold PBS; and lysed with SDS lysis buffer containing 1% SDS, 10 mM Tris (pH7.4), 10 mM NaF, 100 μM $Na_3VO_4$, 2 mM EDTA, 2 mM benzamidine and 1 mM PMSF. JNKs activity was assayed by Western blotting using an antibody specific for phosphorylated JNK to detect phosphorylated (active) JNKs[17,20,23]. Whole cell lysates were boiled for 5 min and centrifuged at 10,000×g for 10 min, and the supernatants were used for Western blotting. Protein was measured using the Bio-Rad Coomassie Blue assay. The proteins were resolved on 8% SD S-PAGE and transferred to PVDF membrane (Millipore, Bedford, Mass.). Blots were incubated with the primary antibodies (Cell Signaling Technology, Inc) anti-phospho-JNK, anti-JNK, anti-HA (6E2) (1:1000 to 1:5000), followed by appropriate HRP-conjugated secondary antibodies. Protein bands were detected by enhanced chemiluminescence (ECL, Pierce), followed by exposure to x-ray film. To quantify phospho-JNKs, serial dilutions of anisomycin (1 µg/ml)-stimulated HEK-A cell lysates were used to ensure that all samples were in linear range. The values for these proteins are expressed in arbitrary units.

References Cited in This Example

1 Lim, W. A. Designing customized cell signalling circuits. *Nat Rev Mol Cell Biol* 11, 393-403 (2010).
2 Burack, W. R. & Shaw, A. S. Signal transduction: hanging on a scaffold. *Curr Opin Cell Biol* 12, 211-216 (2000).
3 Dhanasekaran, D. N., Kashef, K., Lee, C. M., Xu, H. & Reddy, E. P. Scaffold proteins of MAP-kinase modules. *Oncogene,* 3185-3202 (2007).
4 Keshet, Y. & Seger, R. The MAP kinase signaling cascades: a system of hundreds of components regulates a diverse array of physiological functions. *Methods Mol Biol* 661, 3-38 (2010).
5 Widmann, C., Gibson, S., Jarpe, M. B. & Johnson, G. L. Mitogen-activated protein kinase: conservation of a three-kinase module from yeast to human. *Physiol Rev* 79, 143-180 (1999).
6 Good, M. C., Zalatan, J. G. & Lim, W. A. Scaffold proteins: hubs for controlling the flow of cellular information. *Science* 332, 680-686 (2011).
7 Davis, R. J. Signal transduction by the JNK group of MAP kinases. *Cell* 103, 239-252 (2000).
8 Sabapathy, K. Role of the JNK pathway in human diseases. *Prog Mol Biol Transl Sci* 106, 145-169 (2012).
9 Flemming, A. Alzheimer's Disease: JNK3 as new target in AD? *Nat Rev Drug Discov* 11, 829 (2012).
10 Yoon, S. O. et al. JNK3 perpetuates metabolic stress induced by Aβ peptides. *Neuron* 75, 824-837 (2012).
11 Lawler, S., Fleming, Y., Goedert, M. & Cohen, P. Synergistic activation of SAPK1/JNK1 by two MAP kinase kinases in vitro. *Curr Biol* 8, 1387-1390 (1998).
12 Yasuda, J., Whitmarsh, A. J., Cavanagh, J., Sharma, M. & Davis, R. J. The JIP group of mitogen-activated protein kinase scaffold proteins. *Mol Cell Biol* 19, 7245-7254 (1999).
13 Gurevich, V. V. & Gurevich, E. V. The structural basis of arrestin-mediated regulation of G protein-coupled receptors. *Pharm Ther* 110, 465-502 (2006).
14 Carman, C. V. & Benovic, J. L. G-protein-coupled receptors: turn-ons and turn-offs. *Curr Opin Neurobiol* 8, 335-344 (1998).
15 Gurevich, E. V. & Gurevich, V. V. Arrestins are ubiquitous regulators of cellular signaling pathways. *Genome Biol* 7, 236 (2006).
16 McDonald, P. H. et al. Beta-arrestin 2: a receptor-regulated MAPK scaffold for the activation of JNK3. *Science* 290, 1574-1577 (2000).
17 Kook, S. et al. Arrestin-3 binds JNK1α1 and JNK2α2 and facilitates the activation of these ubiquitous JNK isoforms in cells via scaffolding. *J Biol Chem* 288, 37332-37342 (2013).
18 Song, X., Coffa, S., Fu, H. & Gurevich, V. V. How does arrestin assemble MAPKs into a signaling complex? *J Biol Chem* 284, 685-695, doi:M806124200 [pii]10.1074/jbc.M806124200 (2009).
19 Zhan, X., Kaoud, T. S., Dalby, K. N. & Gurevich, V. V. Non-visual arrestins function as simple scaffolds assembling MKK4-JNK3α2 signaling complex. *Biochemistry* 50, 10520-10529 (2011).
20 Zhan, X., Kaoud, T. S., Kook, S., Dalby, K. N. & Gurevich, V. V. JNK3 binding to arrestin-3 differentially affects the recruitment of upstream MAP kinase kinases. *J Biol Chem* 288, 28535-28547 (2013).
21 Miller, W. E. et al. Identification of a motif in the carboxyl terminus of beta-arrestin2 responsible for activation of JNK3. *J Biol Chem* 276, 27770-27777 (2001).
22 Song, X., Raman, D., Gurevich, E. V., Vishnivetskiy, S. A. & Gurevich, V. V. Visual and both non-visual arrestins in their "inactive" conformation bind JNK3 and Mdm2 and relocalize them from the nucleus to the cytoplasm. *J Biol Chem* 281, 21491-21499 (2006).
23 Zhan, X., Perez, A., Gimenez, L. E., Vishnivetskiy, S. A. & Gurevich, V. V. Arrestin-3 binds the MAP kinase JNK3α2 via multiple sites on both domains. *Cell Signal* 26, 766-776 (2014).
24 Breitman, M. et al. Silent scaffolds: inhibition of c-Jun N-terminal kinase 3 activity in the cell by a dominant-negative arrestin-3 mutant. *J Biol Chem* 287, 19653-19664 (2012).
25 Levchenko, A., Bruck, J. & Sternberg, P. W. Scaffold proteins may biphasically affect the levels of mitogen-activated protein kinase signaling and reduce its threshold properties. *Proc Natl Acad Sci USA* 97, 5818-5823 (2000).
26 Levchenko, A., Bruck, J. & Sternberg, P. W. Regulatory modules that generate biphasic signal response in biological systems. *Syst Biol (Stevenage)* 1, 139-148 (2004).
27 Zhan, X., Gimenez, L. E., Gurevich, V. V. & Spiller, B. W. Crystal structure of arrestin-3 reveals the basis of the difference in receptor binding between two non-visual arrestins. *J Mol Biol* 406, 467-478 (2011).
28 Sutton, R. B. et al. Crystal Structure of Cone Arrestin at 2.3 Å: Evolution of Receptor Specificity. *J Mol Biol* 354, 1069-1080 (2005).
29 Han, M., Gurevich, V. V., Vishnivetskiy, S. A., Sigler, P. B. & Schubert, C. Crystal structure of beta-arrestin at 1.9 A: possible mechanism of receptor binding and membrane translocation. *Structure* 9, 869-880 (2001).
30 Hirsch, J. A., Schubert, C., Gurevich, V. V. & Sigler, P. B. The 2.8 A crystal structure of visual arrestin: a model for arrestin's regulation. *Cell* 97, 257-269 (1999).
31 Ahmed, M. R. et al. Ubiquitin ligase parkin promotes Mdm2-arrestin interaction but inhibits arrestin ubiquitination. *Biochemistry* 50, 3749-3763 (2011).
32 Hanson, S. M. et al. Arrestin mobilizes signaling proteins to the cytoskeleton and redirects their activity. *J Mol Biol* 368, 375-387 (2007).
33 Seo, J., Tsakem, E. L., Breitman, M. & Gurevich, V. V. Identification of arrestin-3-specific residues necessary for JNK3 activation. *J Biol Chem* 286, 27894-27901 (2011).
34 Sterne-Marr, R. et al. Polypeptide variants of beta-arrestin and arrestin3. *J Biol Chem* 268, 15640-15648 (1993).
35 Kim, M. et al. Conformation of receptor-bound visual arrestin. *Proc Nat Acad Sci USA* 109, 18407-18412 (2012).

36 Zhuang, T. et al. Involvement of Distinct Arrestin-1 Elements in Binding to Different Functional Forms of Rhodopsin. *Proc Nat Acad Sci USA* 110, 942-947 (2013).

37 Kang, Y. et al. Crystal structure of rhodopsin bound to arrestin determined by femtosecond X-ray laser. *Nature* 523, 561-567 (2015).

38 Luttrell, L. M. et al. Activation and targeting of extracellular signal-regulated kinases by beta-arrestin scaffolds. *Proc Natl Acad Sci USA* 98, 2449-2454 (2001).

39 Bruchas, M. R., Macey, T. A., Lowe, J. D. & Chavkin, C. Kappa opioid receptor activation of p38 MAPK is GRK3- and arrestin-dependent in neurons and astrocytes. *J Biol Chem* 281, 18081-18089 (2006).

40 Zhan, X. et al. Arrestin-3-Dependent Activation of c-Jun N-Terminal Kinases (JNKs). *Curr Protoc Pharmacol* 68, 2.12.11-12.12.26 (2015).

41 Els, S., Beck-Sickinger, A. G. & Chollet, C. Ghrelin receptor: high constitutive activity and methods for developing inverse agonists. *Methods Enzymol* 485, 103-121 (2010).

Figure 6:
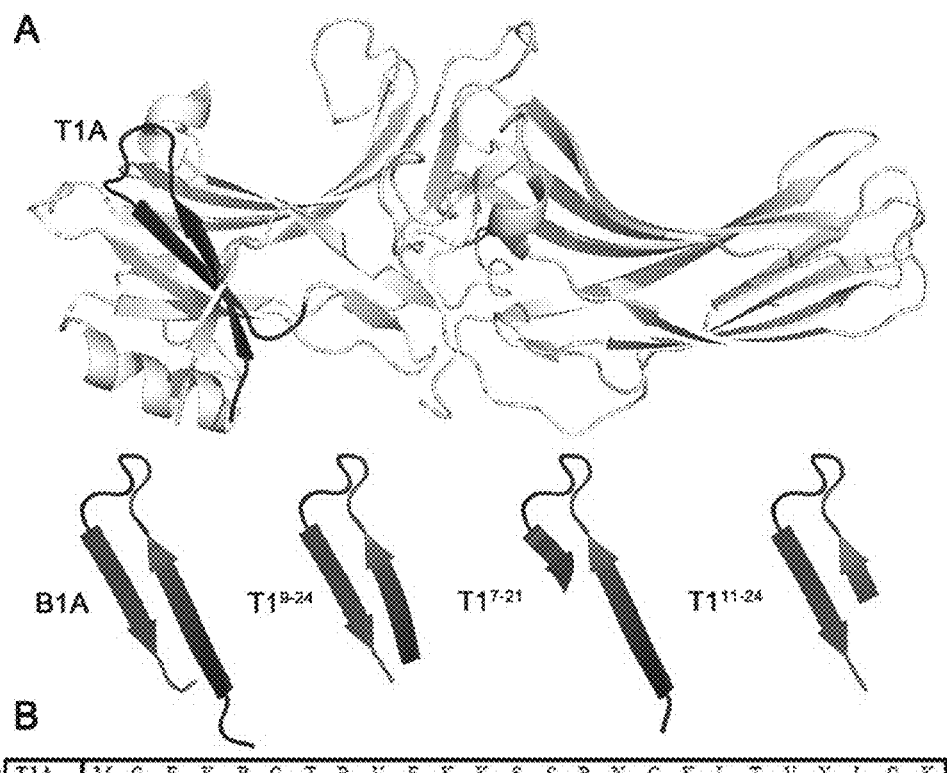
FIG. 6. Schematic of T1A, T1A-derived peptides, and B1A. A) The constructed T1A-derived peptides and B1A (homologous region for T1A obtained from arrestin-2) displayed next to arrestin-3 basal structure (PDB 3P2D (21)). B) T1A consists of the first twenty-five amino acids of arrestin-3, which are shown using the one-letter amino acid code. Note that the three-dimensional structure of the peptides is not known and it is likely that they do not retain the structure of the full-length protein. T1A sequence shown is SEQ ID NO:1. B1A sequence shown is SEQ ID NO:6. T1$^{9-24}$ sequence shown is SEQ ID NO:4. T1$^{7-21}$ sequence shown is SEQ ID NO:3. T1$^{11-24}$ sequence shown is SEQ ID NO:2.

Example 2. Identification of Novel Arrestin-3 Derived Peptides that Facilitate or Inhibit JNK Activity As discussed in Example 1 above, the first 25 residues of arrestin-3 contained in the T1A peptide are primarily responsible for the ability of arrestin-3 to scaffold the ASK1-MKK4/7-JNK3 signaling module. These data identify a relatively short arrestin-3-derived peptide as an effective scaffold of the ASK1-MKK4/7-JNK3 signaling cascade. As T1A was already the smallest MAPK scaffold known at the time, it was unknown whether even smaller peptides yet could act as a scaffold. To test this, the inventors constructed T1A-derived peptides and B1A-derived peptides (homologous region for T1A obtained from arrestin-2). These are shown in FIG. 6A displayed next to arrestin-3 basal structure (PDB 3P2D). T1A consists of the first twenty-five amino acids of arrestin-3, which are shown using the one-letter amino acid code in FIG. 6B, and are also shown below:

```
                                            (SEQ ID NO: 1)
T1A (arrestin-3)      MGEKPGTRVFKKSSPNCKLTVYLGK (SEQ ID NO: 2)
T1A14 (T1(11-24))     KKSSPNCKLTVYLG (SEQ ID NO: 3)
T1A15 (T1(7-21))      TRVFKKSSPNCKLTV (SEQ ID NO: 4)
T1A16 (T1(9-24))      VFKKSSPNCKLTVYLG (SEQ ID NO: 5)
T1A13 (T1(9-21))      VFKKSSPNCKLTV (SEQ ID NO: 6)
B1A (arrestin-2)      MGDK-GTRVFKKASPNGKLTVYLGK
```

Differences between arrestin-3 and arrestin-2 (B1A) are highlighted in gray. Both T1A and B1A are the N-terminal peptides of their respective arrestins. These are bovine arrestin sequences. N-terminal sequence of all mammalian arrestin-3 is identical. Note that the three-dimensional structure of the peptides is not known and it is likely that they do not retain the structure of the full-length protein. The full length arrestin-3 (bovine) sequence is as follows:

```
Arrestin-3 (bovine) full sequence (SEQ ID NO: 7):
MGEKPGTRVF KKSSPNCKLT VYLGKRDFVD HLDKVDPVDG
VVLVDPDYLK DRKVFVTLTC AFRYGREDLD VLGLSFRKDL
FIANYQAFPP TPNPPRPPTR LQERLLRKLG QHAHPFFFTI
PQNLPCSVTL QPGPEDTGKA CGVDFEIRAF CAKSLEEKSH
KRNSVRLVIR KVQFAPEKPG PQPSAETTRH FLMSDRSLHL
EASLDKELYY HGEPLNVNVH VTNNSTKTVK KIKVSVRQYA
DICLFSTAQY KCPVAQVEQD DQVSPSSTFC KVYTITPLLS
NNREKRGLAL DGKLKHEDTN LASSTIVKEG ANKEVLGILV
SYRVKVKLVV SRGGDVSVEL PFVLMHPKPH DHIALPRPQS
AATHPPTLLP SAVPETDAPV DTNLIEFETN YATDDDIVFE
DFARLRLKGL KDEDYDDQFC
```

Figure 7:
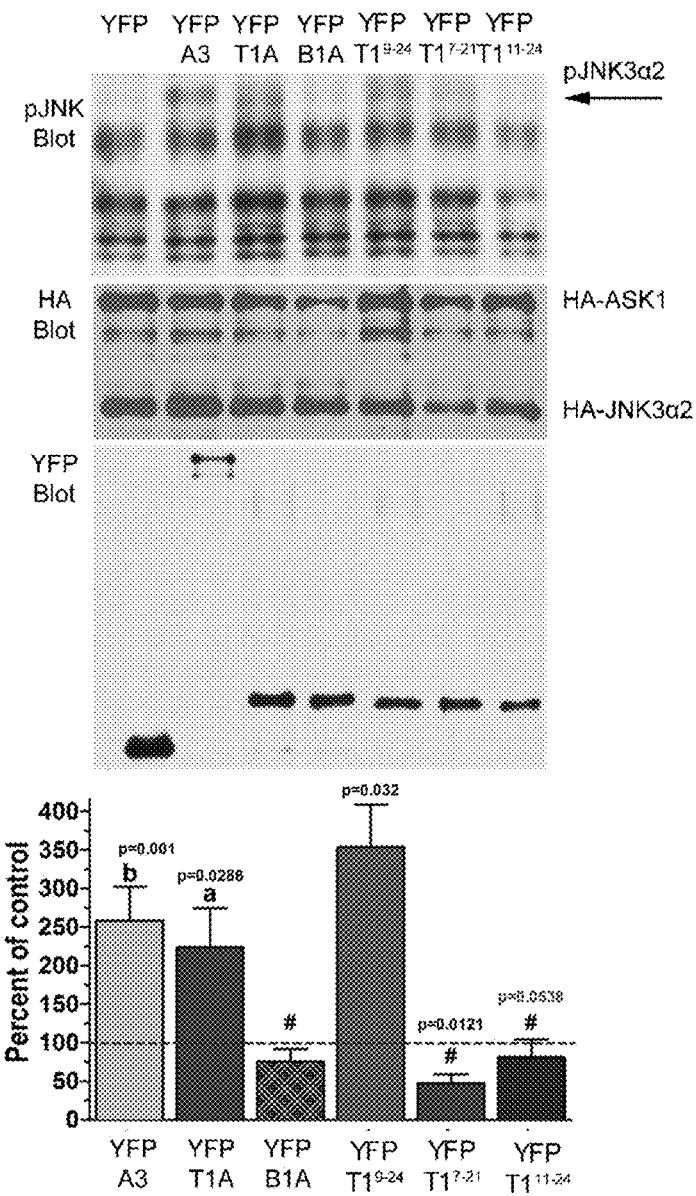
FIG. 7. In cell JNK3 Activation Assay. COS7 cells were transfected with HA-ASK1, HA-JNK3α2, and YFP-arrestin constructs to measure in cell JNK3α2 activation. Phospho-JNK3 is shown as the uppermost band in the Western analysis, and was analyzed by densitometric quantification using Quantity One software (quantification in bottom panel). Western analysis was used to demonstrate equal expression of HA-ASK1, HA-JNK3α2, and the YFP-arrestin constructs. The data were statistically analyzed by ANOVA with protein as the main factor. Significance of the difference from control (p values) is indicated. Note that T1(9-24) facilitates JNK3 activation, similar to T1A and full-length arrestin-3, whereas T1(7-21) inhibits it.

The JNK3 activation was next tested in cells (See FIG. 7). COS7 cells were transfected with HA-ASK1, HA-JNK3α2, and YFP-arrestin constructs to measure in cell JNK3α2 activation. Phospho-JNK3 is shown as the uppermost band in the Western analysis, and was analyzed by densitometric quantification using Quantity One software (quantification in bottom panel). Western analysis was used to demonstrate equal expression of HA-ASK1, HA-JNK3α2, and the YFP-arrestin constructs. The data were statistically analyzed by ANOVA with protein as the main factor. Significance of the difference from control (p values) is indicated. Note that T1(9-24) facilitates JNK3 activation, similar to T1A and full-length arrestin-3. Unexpectedly, T1(7-21) was found to inhibit JNK3 activation.

In *Cell* JNK3 Activation Assay COS7 African green monkey cells were sustained in DMEM solution containing 10% heat-inactivated FBS (Invitrogen), penicillin, and streptomycin at 37° C. and 5% $CO_2$. Cells were transfected at 90-100% confluency in 6-well plates with pcDNA3-HA-ASK1 (0.4 ug), pcDNA3-HA-JNK3α2 (0.2 ug), and pcDNA3-Venus arrestin constructs (0.2-0.6 ug) at a 1:2 ratio of DNA:Lipofectamine 2000 (Invitrogen). At 48 hrs post-transfection, the cells were incubated with phosphatase inhibitors (20 mM NaF and 1 mM $Na_3VO_4$) in PBS for 15 mins, washed twice with cold PBS, and lysed using 50 mM Tris (pH 7.8), 2 mM EDTA, 250 mM NaCl, 10% Glycerol, 0.5% NP-40, 2 mM benzamide, and 1 mM PMSF. Protein concentration was measured using the Bio-Rad Quick Start™ Bovine Serum Albumin (BSA) Standard Set. The proteins were subjected to 10% SDS-PAGE and transferred to PVDF membrane (Millipore, Bedford, Mass.). Membranes were incubated with respective primary antibodies (Cell Signaling Technology, Inc.) anti-ASK1 (#3762S), anti-phospho-JNK (#9251), anti-SAPK/JNK (#9252P), anti-GST (#2625), or anti-HA (#3724), followed by the appropriate HRP-conjugated secondary antibodies. Bands were detected by x-ray film using enhanced chemiluminescence (ECL, Pierce) and quantification was done using the software Quantity One (BioRad).

Example 3. Characterization of Novel Arrestin-3 Derived Peptides

Figure 8:
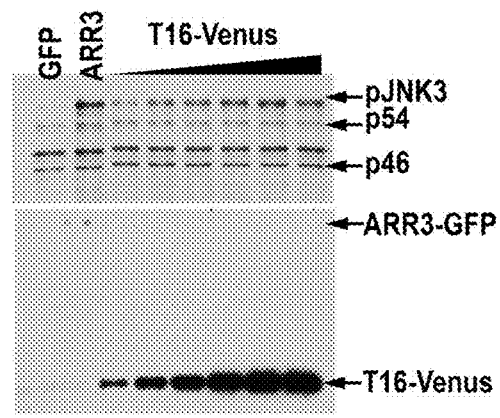
FIG. 8. The ARR3-derived T1A16 peptide is capable of activating the JNK pathway. Representative Western blots show activation of JNK3 in Cos7 cells by ARR3-derived peptide T1A16. Upper panel—increasing concentrations of T1A16 caused increasing JNK activation (most evident for HA-JNK3α2). Lower panel—expression of ARR3-GFP and T1A16-Venus.
Figure 9:
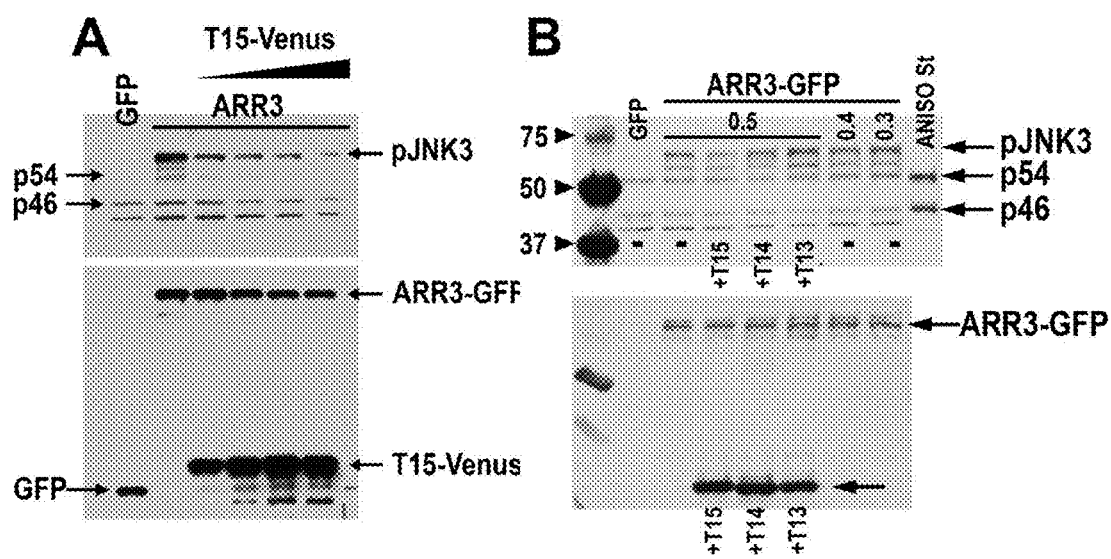
FIG. 9. The ARR3-derived T1A15 peptide is capable of reducing ARR3-dependent activation of the JNK pathway. (A) Dose-dependent action of Venus-T1A15 on the JNK activity. Upper blot panel—T1A15 was expressed at increasing concentration with full-length ARR3. Cells expressing GFP (negative control) and full-length ARR3 only (positive control) are shown for comparison. Note the reduced activity of HA-JNK3α2 expressed in the cells as well as that of endogenous JNK isoforms (p54 and p46 bands). The lower panels show corresponding expression of GFP, full-length ARR3 and increasing concentrations of Venus-T1A15. (B) Comparison of the activity of shorter ARR3-derived peptides. Three shorter peptides, T1A15, T1A14, and T1A13, were co-expressed with full-length ARR3, and the JNK activity assessed by western blot. ARR3 induced the JNK activation, which was effectively suppressed by T1A15. T1A14 was marginally effective, whereas T1A13 had no effect. Lower panel shows corresponding expression of the peptides and that of full-length ARR3.

First, the action of arrestin-3-derived peptides expressed in cultured cells on JNK3 activity was investigated. It was shown that arrestin-3-derived peptide T1A16 (T1A16 is also referred to as T16 herein) expressed in cultures Cos7 cells dose-dependently activates JNK3 (FIG. 8). In contrast, a smaller peptide T1A15 (T1A15 is also referred to as T15 herein) acts as dominant negative reducing arrestin-3-dependent activation of JNK3 as well as other JNK isoforms in a dose dependent manner (FIG. 9).

Next, arrestin-3-derived peptides T1A16 and T1A15 were investigated for activity in the animal model of L-DOPA-induced dyskinesia. It was shown that the peptides expressed as Venus fusions in the motor striatum of hemiparkinsonian mice via lentivirus-mediated gene transfer modulate the manifestations of L-DOPA-induced dyskinesia (LID). The mice lacking ARR3 have reduced LID, and restoration of ARR3 into the motor striatum via lentivirus-mediated gene transfer rescues LID in these animals. Here, it was demonstrated that T1A16 mimics the action of full-length ARR3 in this behavioral model.

Figure 10:
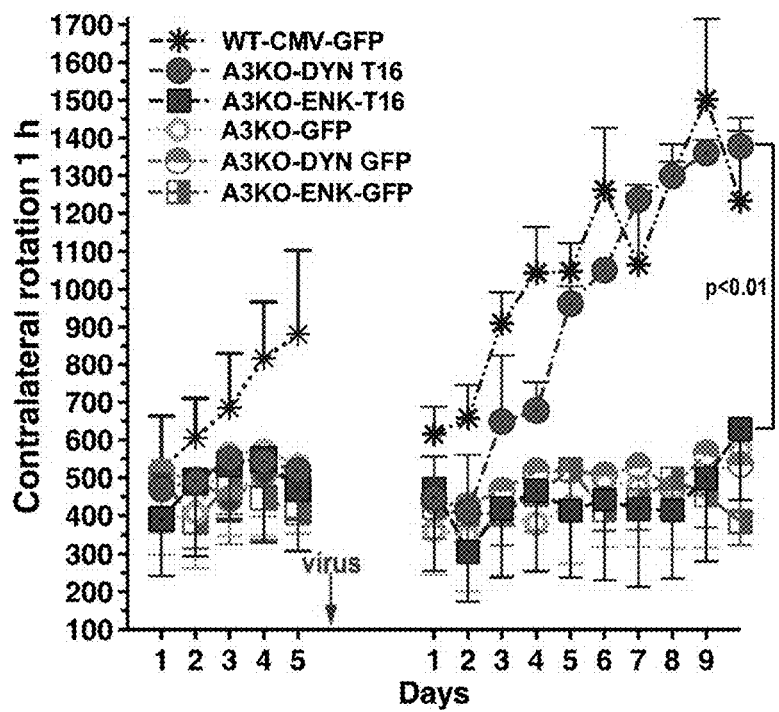
FIG. 10. Rescue of L-DOPA-induced rotations in ARR3 KO mice by T1A16. Data are shown as means±S.E.M. Mice were pre-tested for L-DOPA-induced rotations before receiving lentiviruses. Respective lentiviruses were injected into the dorsolateral striatum of ARR3 KO mice. WT mice received GFP. Note that before the virus injection all ARR3 KO groups showed low rate of behavioral sensitization to L-DOPA, whereas WT mice showed higher rotational frequency. The arrestin-3-derived peptide T1A16 selectively expressed in striatonigral MSNs under control of the dynorphine (DYN) promoter fully rescued rotations in A3KO mice. In contrast, selective expression of T1A16 in striatopallidal MSNs under control of the enkephaline (ENK) promoter was ineffective. Mice expressing GFP under DYN, ENK, or CMV (ARR3-GFP) promoters showed similar low performance. Significance levels are by Bonferroni post hoc test across all testing sessions.

The mice were rendered hemiparkinsonian by the unilateral injection of the dopaminergic neurotoxin 6-hydroxydopamine. Such animals develop contralateral rotations of increasing frequency in response to repeated administration of L-DOPA. ARR3 knockout mice (KO) have lower propensity than wild type (WT) animals to such rotations. The expression of T1A16 in the striatum of ARR3 KO mice fully restores rotations in ARR3 KO mice to the level of that in WT mice (FIG. 10).

Figure 11:
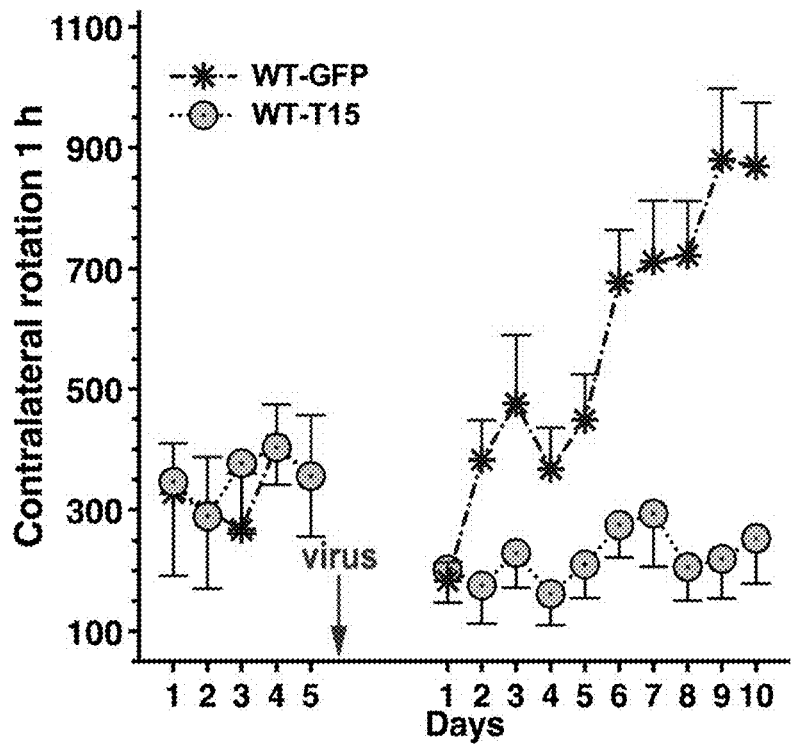
FIG. 11. Inhibition of L-DOPA-induced rotations in WT mice by ARR3-derived peptide T1A15 inhibiting JNK3. The arrestin-3-derived peptide T1A15 expressed under CMV promoter in striatal neurons inhibited rotations in WT mice as compared to WT mice expressing GFP.

A similar experiment conducted in WT hemiparkinsonian mice expressing either GFP (control) or T1A15 under generic CMV promoter demonstrated that T1A15 was able to suppress the rotational behavior (FIG. 11), showing the use of this peptide for anti-LID therapy.

Next, cell-penetrating analogues of arrestin-3-derived peptides T1A16 and T1A15 were constructed to be used in in vitro and in vivo experiments (FIG. 12). As shown here, these cell-permeable modified peptides retain the ability to modulate the JNK activity and are able to enter neurons in the brain.

The ability of these peptides to enter cultured cells was examined. FIG. 13A shows a Neuro2A cell labeled with T1A16 cell-penetrating peptide (cpT1A16) tagged with fluorescein. Untagged cpT1A16 and cpT1A15 were used to examine their ability to activate and inhibit, respectively, the JNK activity in cultured HEK-A cells lacking arrestins (which had been removed using CRISPR technology) ([2]).

In order to evaluate the ability of cpT1A16 and cpT1A15 to enter neurons in the mouse brain, the peptides conjugated with fluorescein were injected into the mouse striatum, and observed the native fluorescence 3 days later. Numerous neurons containing FL were observed along the injection track and throughout the striatum. An alternative injection route more amenable for therapeutic applications (intranasal injection) was also tested. It was found that the peptides injected intranasally were able to enter the striatum and were detected in the striatal neurons, albeit at a much lower concentration than following the direct striatal injection (FIG. 14).

References Cited in This Example

[1] S. Lim, W.-J. Kim, Y.-H. Kim, S. Lee, J.-H. Koo, J.-A. Lee, H. Yoon, D.-H. Kim, H.-J. Park, H.-M. Kim, H.-G. Lee, J. Yun Kim, J.-U. Lee, J. Hun Shin, L. Kyun Kim, J. Doh, H. Kim, S.-K. Lee, A. L. M. Bothwell, M. Suh, J.-M. Choi, dNP2 is a blood-brain barrier-permeable peptide enabling ctCTLA-4 protein delivery to ameliorate experimental autoimmune encephalomyelitis, 6 (2015) 8244.

[2] E. Alvarez-Curto, A. Inoue, L. Jenkins, S. Z. Raihan, R. Prihandoko, A. B. Tobin, G. Milligan, Targeted Elimination of G Proteins and Arrestins Defines Their Specific Contributions to Both Intensity and Duration of G Protein-coupled Receptor Signaling, Journal of Biological Chemistry 291(53) (2016) 27147-27159.

[3] S. Kook, X. Zhan, T. S. Kaoud, K. N. Dalby, V. V. Gurevich, E. V. Gurevich, Arrestin-3 binds JNK1 and JNK2 and facilitates the activation of these ubiquitous JNK isoforms in cells via scaffolding, J Biol Chem 288 (2014) 37332-37242.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A composition comprising a pharmaceutically acceptable carrier and an isolated polypeptide consisting of the amino acid sequence set forth in SEQ ID NO:3.

2. The composition of claim 1, wherein the polypeptide is linked to a second polypeptide, wherein the second polypeptide improves cell permeability of the polypeptide.

3. The composition of claim 2, wherein the second polypeptide comprises the amino acid sequence set forth in SEQ ID NO:20.

4. The composition of claim 1, further comprising an additional therapeutic agent.

* * * * *

UNITED STATES PATENT AND TRADEMARK OFFICE
CERTIFICATE OF CORRECTION

PATENT NO. : 10,369,187 B2
APPLICATION NO. : 15/892853
DATED : August 6, 2019
INVENTOR(S) : Vsevolod V. Gurevich et al.

It is certified that error appears in the above-identified patent and that said Letters Patent is hereby corrected as shown below:

In the Specification

Column 1, under STATEMENT REGARDING FEDERALLY SPONSORED RESEARCH, please amend the paragraph as follows:

Line 15 - "Grant No. R01 GM077561" should read "grant numbers GM077561 and GM109955".

Line 16 - "The Government has certain rights to the" should read "The government has certain rights in the".

Signed and Sealed this
First Day of October, 2019

Andrei Iancu
*Director of the United States Patent and Trademark Office*